(12) United States Patent
Palle et al.

(10) Patent No.: US 7,781,460 B2
(45) Date of Patent: Aug. 24, 2010

(54) SUBSTITUTED INDAZOLES AS INHIBITORS OF PHOSPHODIESTERASE TYPE-IV

(75) Inventors: Venkata Palle, Pune (IN); Sarala Balachandran, Mumbai (IN); Lalit Kumar Baregama, Kapasan (IN); Saswati Chakladar, Delhi (IN); Sarika Ramnani, Lucknow (IN); Nagarajan Muthukamal, Tamil Nadu (IN); Abhijit Ray, New Delhi (IN); Sunanda G. Dastidar, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 12/065,819

(22) PCT Filed: Aug. 30, 2006

(86) PCT No.: PCT/IB2006/002369

§ 371 (c)(1),
(2), (4) Date: Aug. 26, 2008

(87) PCT Pub. No.: WO2007/029077

PCT Pub. Date: Mar. 15, 2007

(65) Prior Publication Data

US 2008/0312285 A1    Dec. 18, 2008

(30) Foreign Application Priority Data

Sep. 5, 2005    (IN)    ........................ 2378/DEL/2005

(51) Int. Cl.

| | |
|---|---|
| A61K 31/443 | (2006.01) |
| A61K 31/416 | (2006.01) |
| A61K 31/422 | (2006.01) |
| A61K 31/427 | (2006.01) |
| C07D 413/04 | (2006.01) |
| C07D 271/06 | (2006.01) |
| C07D 271/10 | (2006.01) |
| C07D 261/04 | (2006.01) |

(52) U.S. Cl. .................. 514/340; 514/364; 514/378; 548/131; 548/143; 548/240; 546/269.4

(58) Field of Classification Search .............. 514/340, 514/364, 378; 546/269.4; 548/131, 143, 548/240

See application file for complete search history.

(56) References Cited

U.S. PATENT DOCUMENTS

| 6,339,099 B1 | 1/2002 | Lam et al. .................... 514/378 |
| 2003/0176421 A1 | 9/2003 | Watson et al. ............. 514/224.2 |

FOREIGN PATENT DOCUMENTS

| EP | 1 040 829 | 10/2000 |
| EP | 1 251 128 | 10/2002 |
| WO | WO 95/14680 | 6/1995 |
| WO | WO 97/48697 | 12/1997 |
| WO | WO 97/49702 | 12/1997 |
| WO | WO 98/09961 | 3/1998 |
| WO | WO 98/57951 | 12/1998 |
| WO | WO 99/23076 | 5/1999 |
| WO | WO 99/23077 | 5/1999 |
| WO | WO 00/59902 | 10/2000 |
| WO | WO 01/12600 | 2/2001 |
| WO | WO 01/19788 | 3/2001 |
| WO | WO 01/19798 | 3/2001 |
| WO | WO 02/50070 | 6/2002 |
| WO | WO 03/047520 | 6/2003 |
| WO | WO 2005/051931 | 6/2005 |
| WO | WO 2006/129158 | 12/2006 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Sutherland and Rall, "The Relation of Adenosine-3',5'-Phosphate and Phosphorylase to the Actions of Catecholamines and Other Hormones", *Pharmacological Reviews*, 12:265-299 (1960).
Beavo and Reifsnyder, "Primary sequence of cyclic nucleotide phosphodiesterase isozymes and the design of selective inhibitors", *Trends in Pharmacological Sciences*, 11:150-155 (1990).

(Continued)

*Primary Examiner*—Kamal A Saeed
*Assistant Examiner*—Samantha L Shterengarts
(74) *Attorney, Agent, or Firm*—James J. DeYonker, Esq

(57) ABSTRACT

The present invention relates to isoxazoline derivatives of structure Ia, which can be used as selective inhibitors of phosphodiesterase (PDE) type IV. Compounds disclosed herein can be useful in the treatment of CNS disorders, AIDS, asthma, arthritis, bronchitis, chronic obstructive pulmonary disease (COPD), psoriasis, allergic rhinitis, shock, atopic dermatitis, Crohn's disease, adult respiratory distress syndrome (ARDS), eosinophilic granuloma, allergic conjunctivitis, osteoarthritis, ulcerative colitis and other inflammatory diseases especially in humans. Processes for the preparation of disclosed compounds are provided, as well as pharmaceutical compositions containing the disclosed compounds, and their use as phosphodiesterase (PDE) type IV inhibitors.

(Ia)

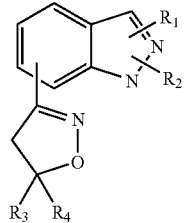

3 Claims, No Drawings

OTHER PUBLICATIONS

Nicholson et al., "Differential modulation of tissue function and therapeutic potential of selective inhibitors of cyclic nucleotide phosphodiesterase isoenzymes", *Trends in Pharmacological Sciences*, 12:19-27 (1991).

Verghese et al., "Anti-Neutrophil Activity of Cyclic Nucleotide Phosphodiesterase Inhibitors with Varying Cardiotonic Potencies", *Journal of Molecular Cell Cardiology*, 21(suppl.II):S61 (1989).

Greene, T.Q. and Wuts, P.G.M., 1991. *Protective Groups in Organic Synthesis*. 2nd Edition. New York: Wiley Interscience Publications.

Burnouf et al., "Synthesis, Structure-Activity Relationships, and Pharmacological Profile of 9-Amino-4-oxo-1-phenyl-3,4,6,7-tetrahydro[1,4]diazepino[6,7,1-*hi*]indoles: Discovery of Potent, Selective Phosphodiesterase Type 4 Inhibitors", *Journal of Medicinal Chemistry*, 43(25):4850-4867 (2000).

* cited by examiner

SUBSTITUTED INDAZOLES AS INHIBITORS OF PHOSPHODIESTERASE TYPE-IV

FIELD OF THE INVENTION

The present invention relates to isoxazoline derivatives, which can be used as selective inhibitors of phosphodiesterase (PDE) type IV.

Compounds disclosed herein can be useful in the treatment of CNS disorders, AIDS, asthma, arthritis, bronchitis, chronic obstructive pulmonary disease (COPD), psoriasis, allergic rhinitis, shock, atopic dermatitis, Crohn's disease, adult respiratory distress syndrome (ARDS), eosinophilic granuloma, allergic conjunctivitis, osteoarthritis, ulcerative colitis and other inflammatory diseases especially in humans.

Processes for the preparation of disclosed compounds are provided, as well as pharmaceutical compositions containing the disclosed compounds, and their use as phosphodiesterase (PDE) type IV inhibitors.

BACKGROUND OF THE INVENTION

It is known that cyclic adenosine-3',5'-monophosphate (cAMP) exhibits an important role of acting as an intracellular secondary messenger (Sutherland, *Pharmacol. Rev*, (1960), 12, 265). Its intracellular hydrolysis to adenosine 5'-monophosphate (AMP) causes number of inflammatory conditions which are not limited to psoriasis, allergic rhinitis, shock, atopic dermatitis, crohn's disease, adult respiratory distress syndrome (ARDS), eosinophilic granuloma, allergic conjunctivitis, osteoarthritis, ulcerative colitis. The most important role in the control of cAMP (as well as of cGMP) levels is played by cyclic nucleotide phosphodiesterases (PDE) which represent a biochemically and functionally, highly variable superfamily of the enzyme; eleven distinct families with more than 25 gene products are currently recognized. Although PDE I, PDE II, PDE III, PDE IV, and PDE VII all use cAMP as a substrate, only the PDE IV and PDE VII types are highly selective for hydrolysis of cAMP. Inhibitors of PDE, particularly the PDE IV inhibitors, such as rolipram or Ro-1724 are therefore known as cAMP-enhancers. Immune cells contain type IV and type III PDE, the PDE IV type being prevalent in human mononuclear cells. Thus the inhibition of phosphodiesterase type IV has been a target for modulation and, accordingly, for therapeutic intervention in a range of disease processes.

The initial observation that xanthine derivatives, theophylline and caffeine inhibit the hydrolysis of cAMP led to the discovery of the required hydrolytic activity in the cyclic nucleotide phosphodiesterase (PDE) enzymes. More recently, distinct classes of PDEs have been recognized (Bervo, *TIPS*, (1990), 11, 150), and their selective inhibition has led to improved drug therapy (Nicholus, et al. *TIPS*, 1991, 12, 19). Thus it was recognized that inhibition of PDE IV could lead to inhibition of inflammatory mediator release (Verghese et. al., *J. Mol. Cell. Cardiol.*, 1989, 12 (Suppl.II), S 61).

WO 03/47520 discloses substituted amino methyl factor Xa inhibitors. U.S. Patent Publication No. 2003176421, and EP 1040829 disclose prokinetic agents for treating gastric hypomotility and related disorders. WO 02/50070 discloses piperidine derivatives as subtype-selective N-methyl-D-aspartate antagonists. EP 1251128 discloses cyclohexylamine derivatives as subtype-selective N-methyl-D-aspartate antagonists. WO 00/59902 discloses aryl sulfonyls as factor Xa inhibitors. WO 01/19798 and WO01/19788 disclose novel compounds as factor Xa inhibitors. WO 99/23076, WO 99/23077 discloses indazole bioisostere replacement of catechol in therapeutically active compounds. WO 97/49702 and WO 98/09961 disclose indazole derivatives and their use as inhibitor of phosphodiesterase type IV and production of tumor necrosis factor (TNF). WO 97/48697 discloses substituted azabicyclo compounds and their use as inhibitors of the production of TNF and cyclic AMP phosphodiesterase. WO 99/57951, U.S. Pat. No. 6,339,099 discloses guanidine mimics as factor Xa inhibitor.

SUMMARY OF THE INVENTION

The present invention provides isoxazoline derivatives, which can be used for the treatment of, but not limited to, CNS disorders, AIDS, asthma, arthritis, bronchitis, chronic obstructive pulmonary disease (COPD), psoriasis, allergic rhinitis, shock, atopic dermatitis, Crohn's disease, adult respiratory distress syndrome (ARDS), eosinophilic granuloma, allergic conjunctivitis, osteoarthritis, ulcerative colitis and other inflammatory diseases, and the processes for the synthesis of these compounds.

Pharmaceutically acceptable salts, pharmaceutically acceptable solvates, enantiomers, diastereomers or N-oxides of these compounds having the same type of activity are also provided.

Pharmaceutical compositions containing the compounds, which may also contain pharmaceutically acceptable carriers or diluents, can be used for the treatment of CNS disorders, AIDS, asthma, arthritis, bronchitis, chronic obstructive pulmonary disease (COPD), psoriasis, allergic rhinitis, shock, atopic dermatitis, Crohn's disease, adult respiratory distress syndrome, eosinophilic granuloma, allergic conjunctivitis, osteoarthritis, ulcerative colitis and other inflammatory diseases.

Other aspects will be set forth in the accompanying description which follows and in part will be apparent from the description or may be learnt by the practice of the invention.

In accordance with one aspect, a compound is provided having the structure of Formula Ia

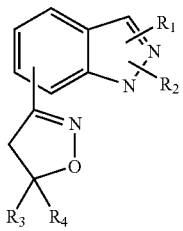

Formula Ia its pharmaceutically acceptable salts, pharmaceutically acceptable solvates, enantiomers, diastereomers or N-oxides wherein $R_1$ and $R_2$ can be independently selected from hydrogen, alkyl, alkenyl, alkynyl, aryl, aralkyl, heteroaryl, heterocyclyl, cycloalkyl, alkoxy, halogen or —OH;

$R_3$ can be alkyl, alkenyl, alkynyl, cycloalkyl, carboxy, heteroaryl, heterocyclyl, aryl, heteroarylalkyl, heterocyclylalkyl, aralkyl or carboxyalkyl; and $R_4$ is cyano, cycloalkyl, aryl, heteroaryl, heterocyclyl, aralkyl, heteroarylalkyl, —CONHNH$_2$, —C(=NOH)NH$_2$ or carboxyalkyl In accordance with another aspect, there is provided a method for treatment or prophylaxis of an animal or a human suffering from inflammatory diseases, comprising administering to a patient in need thereof, an effective amount of a phosphodiesterase type IV inhibitors as described above.

In accordance with a further aspect, there is provided a method for treatment or prophylaxis of an animal or a human suffering from CNS disorders, AIDS, asthma, arthritis, bronchitis, chronic obstructive pulmonary disease (COPD), psoriasis, allergic rhinitis, shock, atopic dermatitis, Crohn's disease, adult respiratory distress syndrome (ARDS), eosinophilic granuloma, allergic conjunctivitis, osteoarthritis, ulcerative colitis and other inflammatory diseases.

In accordance with still another aspect, there are provided processes for preparing the compounds as described above.

A number of the compounds described herein were tested as phosphodiesterase type TV inhibitors. Therefore, pharmaceutical compositions for the possible treatment of diabetes and diabetes-associated complications are provided. In addition, the compounds can be administered orally or parenterally.

The Following Definitions Apply to Terms as Used Herein

The term "alkyl" unless and otherwise specified refers to a monoradical branched or unbranched saturated hydrocarbon chain having from 1 to 20 carbon atoms. Groups such as methyl, ethyl, n-propyl, iso-propyl, n-butyl, iso-butyl, t-butyl, n-pentyl, n-hexyl, n-decyl, tetradecyl, and the like exemplify this term.

It may further be substituted with one or more substituents selected from the groups consisting of alkenyl, alkynyl, alkoxy, cycloalkyl, acyl, thioacyl, acyloxy, cycloalkyloxy, heterocyclyloxy, azido, cyano, halogen, hydroxy, thiol, aryloxy, heteroaryloxy, aminosulfonyl, —$COOR_5$ (wherein $R_5$ is alkyl, aryl, cycloalkyl, heteroaryl, heterocyclyl, aralkyl, heterocyclylalkyl or heteroarylalkyl), —$NHR_x$, —$NH_2$, —$NR_xR_y$, —$C(=O)NR_xR_y$, —$OC(=O)NR_xR_y$, ($R_x$ and $R_y$ are independently selected from $R_5$ or $R_x$ and $R_y$ may together join to form cycloalkyl, heteroaryl or heterocyclyl ring), nitro, —$S(O)_mR_6$ (wherein m is an integer from 0-2 and $R_6$ is alkyl, alkenyl, alkynyl, aryl, cycloalkyl, heteroaryl, heterocyclyl, aralkyl, heterocyclylalkyl, heteroarylalkyl or $NR_xR_y$). Unless otherwise constrained, all substituents may be further substituted by 1-3 substituents chosen from alkyl, —$COOR_5$, —$NHR_x$, —$NH_2$, —$NR_xR_y$, —$C(=O)NR_xR_y$, —$OC(=O)NR_xR_y$, hydroxy, alkoxy, halogen, $CF_3$, cyano and —$S(O)_mR_6$.

Alkyl group as defined above may also be interrupted by 1-5 atoms or groups independently chosen from oxygen, sulfur and —$NR_a$— (where $R_a$ is chosen from hydrogen, alkyl, cycloalkyl, alkenyl, alkynyl, aryl, acyl, aralkyl, —$COOR_5$, —$SO_2R_6$, —$C(=O)NR_xR_y$).

The term "alkenyl" unless and otherwise specified refers to a monoradical of a branched or unbranched unsaturated hydrocarbon group preferably having from 2 to 20 carbon atoms with cis or trans geometry. In the event that alkenyl is attached to the heteroatom, the double bond cannot be alpha to the heteroatom.

It may further be substituted with one or more substituents selected from the group consisting of alkyl, alkynyl, alkoxy, cycloalkyl, acyl, thioacyl, acyloxy, cycloalkyloxy, heterocyclyloxy, heteroaryloxy, —$COOR_5$ (wherein $R_5$ is the same as defined earlier), —$NHR_x$, —$NH_2$, —$NR_xR_y$, —$C(=O)NR_xR_y$, —$OC(=O)NR_xR_y$ (wherein $R_x$ and $R_y$ are the same as defined earlier), azido, cyano, halogen, hydroxy, thiol, aryl, aralkyl, aryloxy, heterocyclyl, heteroaryl, heterocyclylalkyl, heteroarylalkyl, aminosulfonyl, alkoxyamino, nitro, —$S(O)_mR_6$ (wherein $R_6$ and m are the same as defined earlier). Unless otherwise constrained, all substituents may optionally be further substituted by 1-3 substituents chosen from alkyl, —$COOR_5$, hydroxy, alkoxy, halogen, —$CF_3$, cyano, —$NHR_x$, —$NH_2$, —$NH_2$, —$NR_xR_y$, —$C(=O)NR_xR_y$, —$OC(=O))NR_xR_y$ and —$S(O)_mR_6$.

The term "alkynyl" unless and otherwise specified refers to a monoradical of an unsaturated hydrocarbon, preferably having from 2 to 20 carbon atoms.

In the event that alkynyl is attached to the heteroatom, the triple bond cannot be alpha to the heteroatom.

It may further be substituted with one or more substituents selected from the group consisting of alkyl, alkenyl, alkoxy, cycloalkyl, acyl, thioacyl, acyloxy, azido, cyano, halogen, hydroxy, thiol, heteroaryloxy, heterocyclyloxy, cycloalkyloxy, aryl, aralkyl, aryloxy, aminosulfonyl, nitro, heterocyclyl, heteroaryl, heterocyclylalkyl, heteroarylalkyl, —$COOR_5$ (wherein $R_5$ is the same as defined earlier), —$NHR_x$, —$NH_2$, —$NR_xR_y$, —$C(=O)NR_xR_y$, —$OC(=O)NR_xR_y$ (wherein $R_x$ and $R_y$ are the same as defined earlier), —$S(O)_mR_6$ (wherein $R_6$ and m are the same as defined earlier). Unless otherwise constrained, all substituents may optionally be further substituted by 1-3 substituents chosen from alkyl, —$COOR_5$, hydroxy, alkoxy, halogen, —$CF_3$, —$NHR_x$, —$NH_2$, —$NR_xR_y$, —$C(=O)NR_xR_y$, —$C(=O)NR_xR_y$, cyano and —$S(O)_mR_6$.

The term "cycloalkyl" refers to cyclic alkyl groups of from 3 to 20 carbon atoms having a monocyclic ring or polycyclic (fused, spiro or bridged) rings, which may optionally contain one or more olefinic bonds, unless or otherwise constrained. Such cycloalkyl groups include, by way of example, monocyclic structures such as cyclopropyl, cyclobutyl, cyclopentyl, cyclohexyl, cycloheptyl, cyclooctyl, and the like, or polycyclic ring structures such as, tricyclo[3.3.1.1]decane, bicyclo[2.2.2]octane, bicyclo[4.4.0]decane, bicyclo[4.3.0]nonane, bicyclo[3.3.0]octane, bicyclo[2.2.1]heptane and the like, or cyclic alkyl groups to which is fused an aryl group, for example indane, and the like.

It may further be substituted with one or more substituents selected from the group consisting of alkyl, alkenyl, alkynyl, alkoxy, cycloalkyl, acyl, thioacyl, acyloxy, heteroaryloxy, heterocyclyloxy, azido, cyano, halogen, hydroxy, thiol, aryl, aralkyl, aryloxy, aminosulfonyl, —$COOR_5$ (wherein $R_5$ is the same as defined earlier), —$NHR_x$, —$NH_2$, —$NR_xR_y$, —$C(=O)NR_xR_y$, —$OC(=O)NR_xR_y$ (wherein $R_x$ and $R_y$ are the same as defined earlier), nitro, heterocyclyl, heteroaryl, heterocyclylalkyl, heteroarylalkyl, $S(O)_mR_6$ (wherein $R_6$ and m are the same as defined earlier). Unless otherwise constrained, all substituents may optionally be further substituted by 1-3 substituents chosen from alkyl, hydroxy, alkoxy, halogen, $CF_3$, —$NHR_x$—$NH_2$, —$NR_xR_y$, —$C(=O)NR_xR_y$, —$OC(=O)NR_xR_y$, cyano and —$S(O)_mR_6$.

The term "aralkyl" refers to aryl linked through alkyl portion and the said alkyl portion contains carbon atoms from 1-6 and aryl is the same as defined below.

The examples of aralkyl groups are benzyl and the like.

The term "aryl" herein refers to a carbocyclic aromatic group for example, phenyl, naphthyl or anthryl ring and the like optionally substituted with 1 to 3 substituents selected from the group consisting of halogen (F, Cl, Br, I), hydroxy, —$COOR_5$ (wherein $R_5$ is the same as defined earlier), alkyl, alkenyl, alkynyl, cycloalkyl, alkoxy, heterocyclyloxy, heteroaryloxy, cycloalkyloxy, acyl, thioacyl, aryloxy, cyano, nitro, $-NR_xR_y$, $-C(=O)NR_xR_y$, $-NHR_x$, $-NH_2$, $-(SO)_mR_6$ (wherein $R_6$, $R_x$, $R_y$ and m are the same as defined earlier), aryl, heterocyclyl, heteroaryl, heterocyclylalkyl or heteroarylalkyl. The said aryl group may optionally be fused with cycloalkyl group, heteroaryl group or heterocyclyl group.

The term "aryloxy" denotes the group O-aryl wherein aryl is the same as defined above.

The term "heteroaryl" unless and otherwise specified refers to an aromatic monocyclic or polycyclic (fused, spiro or bridged) ring system containing 1-8 heteroatom(s) independently selected from the group consisting of N, O and S. The said heteroaryl ring is optionally substituted with 1 to 3 substituent(s) selected from the group consisting of halogen, hydroxy, alkyl, alkenyl, alkynyl, cycloalkyl, heteroaryl, heterocyclyl, aryloxy, cycloalkyloxy, acyl, thioacyl, $-COOR_5$ (wherein $R_5$ is the same as defined earlier), aryl, alkoxy, aralkyl, cyano, nitro, $-NHR_x$, $-NH_2$, $-NR_xR_y$, $-C(=O)NR_xR_y$, $S(O)_mR_6$, $-OC(=O)NR_xR_y$ (wherein m, $R_6$, $R_x$ and $R_y$ are the same as defined earlier). Unless otherwise constrained, the substituents are attached to the ring atom, be it carbon or heteroatom.

Examples of heteroaryl groups are pyridinyl, pyridazinyl, pyrimidinyl, pyrrolyl, oxazolyl, thiazolyl, thienyl, carbazolyl, isobenzofuranyl, thianthrene, isoxazolyl, triazinyl, furanyl, benzofuranyl, indolyl, benzothiazolyl, benzoxazolyl, imidazolyl, tetrazolyl, quinolinyl, isoquinolinyl, quinazolinyl, benzoxazinonyl, benzothiazinonyl and the like.

The term "heterocyclyl" unless and otherwise specified refers to nonaromatic monocyclic or polycyclic ring (fused, spiro or bridged) system having 1 to 8 heteroatoms selected from the group consisting of O, S and N. For heterocycles containing sulphur, the oxidized sulphur heterocycles containing SO or $SO_2$ are also included. The said heterocyclyl ring system is optionally benzofused or fused with heteroaryl and/or are optionally substituted wherein the substituents are selected from the group consisting of halogen, hydroxy, alkyl, alkenyl, alkynyl, cycloalkyl, acyl, thioacyl, aryl, alkoxy, aralkyl, heteroaryl, heterocyclyl, heteroarylalkyl, heterocyclylalkyl, aryloxy, cyano, nitro, $-COOR_5$ (wherein $R_5$ is the same as defined earlier), $-C(=O)NR_xR_y$, $S(O)_mR_6$, $-OC(=O)NR_xR_y$, $-NHR_x$, $-NH_2$, $-NR_xR_y$ (wherein m, $R_x$ and $R_y$ are the same as defined earlier). Unless or otherwise constrained, the substituents are attached to the ring atom, be it carbon or heteroatom. Also, unless or otherwise constrained the said heterocyclyl ring may optionally contain one or more olefinic bond(s).

Examples of heterocyclyl groups are tetrahydrofuranyl, dihydrofuranyl, dihydropyridinyl, dihydrobenzofuryl, azabicyclohexyl, dihydroindolyl, piperidinyl, isoxazolinyl, thiazolinyl, thiazolidinonyl, oxazolinyl or oxazolidinonyl.

The term "Heteroarylalkyl" refers to heteroaryl group linked through alkyl portion, wherein the alkyl and heteroaryl are the same as defined earlier.

The term "Heterocyclylalkyl" refers to heterocyclyl group linked through alkyl portion, wherein the alkyl and heterocyclyl are the same as defined earlier.

The term "acyl" refers to $-C(=O)R''$ wherein R" is selected from the group alkyl, cycloalkyl, aryl, aralkyl, heteroaryl, heterocyclyl, heteroarylalkyl or heterocyclylalkyl.

The term "thioacyl" refers to $-C(=S)R''$ wherein R" is the same as defined above;

The term "halogen" refers to fluorine, chlorine, bromine or iodine;

The term "leaving group" generally refers to groups that exhibit the desirable properties of being labile under the defined synthetic conditions and also, being easily separated from synthetic products under defined conditions. Examples of such leaving groups includes but not limited to hal (Cl, Br, I), triflate, tosylate, 4-bromophenylsulfonate, 4-nitrophenylsulfonate, mesylate and the like.

The term "Protecting groups" is used herein to refer to known moieties which have the desirable property of preventing specific chemical reaction at a site on the molecule undergoing chemical modification intended to be left unaffected by the particular chemical modification. Also the term protecting group, unless or other specified may be used with groups such as hydroxy, amino, carboxy and examples of such groups are found in T. W. Greene and P. G. M. Wuts, "Protective groups in organic synthesis", $2^{nd}$ ED, John Wiley and Sons, New York, N.Y., which is incorporated herein by reference. The species of the carboxylic protecting groups, amino protecting groups or hydroxy protecting group employed is not so critical so long as the derivatised moieties/moiety is/are stable to conditions of subsequent reactions and can be removed at the appropriate point without disrupting the remainder of the molecule.

The compounds of this invention contain one or more asymmetric carbon atoms and thus occur as racemic mixtures, enantiomers and diastereomers. Some compounds may also exist as conformers/rotamers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are envisioned as part of the invention.

The term "pharmaceutically acceptable salts" refers to derivatives of compounds that can be modified by forming their corresponding acid or base salts. Examples of pharmaceutically acceptable salts include, but are not limited to, mineral or organic acids salts of basic residues (such as amines), or alkali or organic salts of acidic residues (such as carboxylic acids), and the like.

DETAILED DESCRIPTION OF THE INVENTION

The compounds of the present invention may be prepared by techniques well known in the art and familiar to a practitioner skilled in art of this invention. In addition, the compounds of the present invention may be prepared, for example, by processes described herein, although such processes are not the only means by which the compounds may be synthesised. Further, the various synthetic steps described herein may be performed in an alternate sequence in order to give the desired compounds.

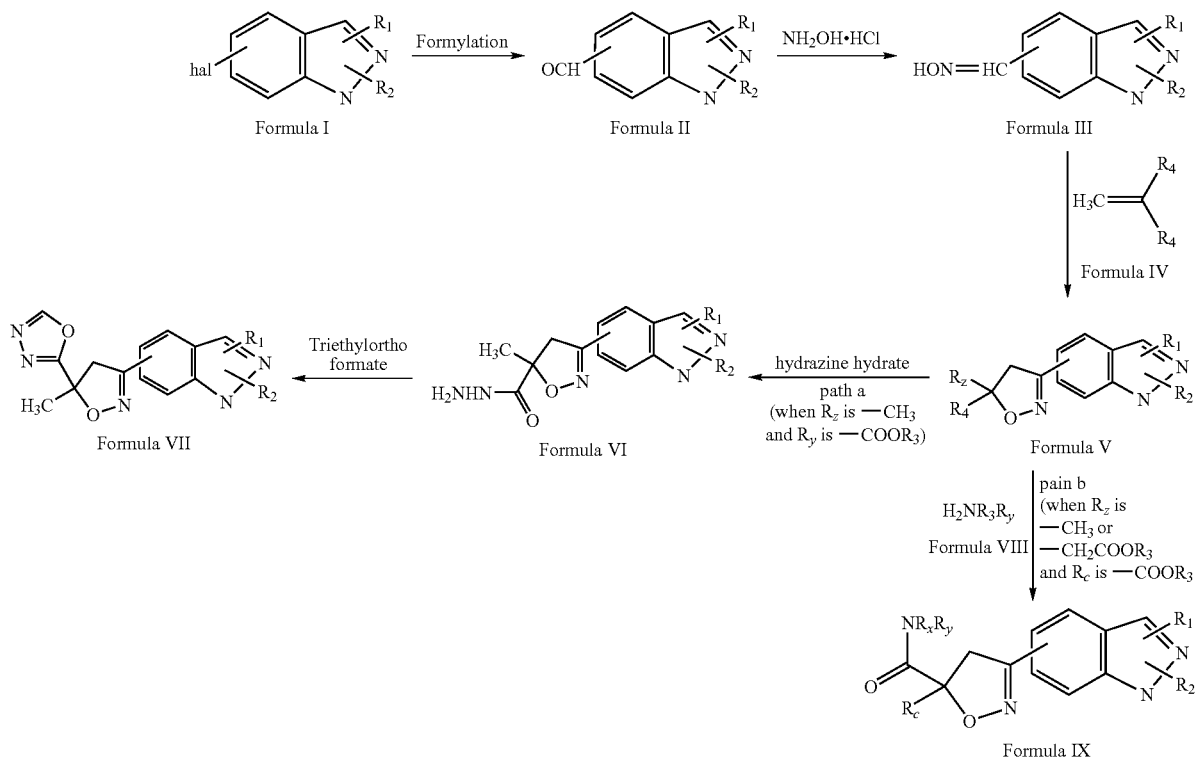

Scheme I

The compounds of Formulae V, VI, VII and IX can be prepared, for example, by following the procedure as described in Scheme I. Thus a compound of Formula I (wherein hal is Br, Cl or I; $R_1$ and $R_2$ are the same as described earlier) can undergo formylation reaction to give a compound of Formula II, which on reaction with hydroxylamine hydrochloride can give a compound of Formula III, which can be reacted with a compound of Formula IV [wherein $R_z$ is alkyl or —$CH_2COOR_5$; $R_q$ is —CN or $COOR_5$ (wherein $R_5$ is the same as defined earlier)] to give a compound of Formula V, path a: the compound of Formula V can be reacted with hydrazine hydrate (when $R_z$ is —$CH_3$ and $R_q$ is $COOR_5$) to give a compound of Formula VI, which can be reacted with triethyl orthoformate to give a compound of Formula VII, or Path b: the compound of Formula V can be reacted with a compound of Formula VIII (wherein $R_x$ and $R_y$ are the same as defined earlier) to give a compound of Formula IX (wherein $R_c$ is —$CH_3$ or $CH_2CONR_xR_y$).

The formylation of a compound of Formula I give a compound of Formula II can be carried out with a formulating agent for example, dimethylformamide, triformamide, tris(diformylamino)methane, tris(dichloromethyl)amine or N,N,N,N-tetraformyl hydrazine in the presence of a base for example, butyl lithium in an organic solvent for example, tetrahydrofuran, dioxane or diethylether. The reaction of a compound of Formula II with hydroxylamine hydrochloride to give a compound of Formula III can be carried out in an organic solvent for example, ethanol, methanol, propanol or isopropylalcohol in the presence of a base for example, sodium acetate, sodium carbonate, ammonium acetate or potassium carbonate.

The compound of Formula V can be reacted with hydrazine hydrate (path a, when $R_z$ is —$CH_3$ and $R_q$ —$CH_2COOR_5$) to give a compound of Formula VI.

The compound of Formula VI can be reacted with triethyl orthoformate to give a compound of Formula IX.

The compound of Formula V can be reacted with a compound of Formula VIII (path b) to give a compound of Formula IX.

Particular illustrative compounds which can be prepared following Scheme I include:

3-(1-Cyclopentyl-1H-indazol-6-yl)-5-methyl-4,5-dihydroisoxazole-5-carbonitrile (Compound No. 1), 3-(1-Cyclopentyl-3-methyl-1H-indazol-6-yl)-5-methyl-4,5-dihydroisoxazole-5-carbonitrile (Compound No. 2), 3-(1-Cyclopentyl-3-ethyl-1H-indazol-6-yl)-5-methyl-4,5-dihydroisoxazole-5-carbonitrile (Compound No. 3), 3-(1-Cyclopentyl-3-methyl-1H-indazol-6-yl)-5-methyl-4,5-dihydroisoxazole-5-carbohydrazide (Compound No. 4)

3-(1-Cyclopentyl-3-ethyl-1H-indazol-6-yl)-5-methyl-4,5-dihydroisoxazole-5-carbohydrazide (Compound No. 5)

1-Cyclopentyl-6-[5-methyl-5-(1,3,4-oxadiazol-2-yl)-4,5-dihydroisoxazol-3-yl]-1H-indazole (Compound No. 6)

1-Cyclopentyl-3-methyl-6-[5-methyl-5-(1,3,4-oxadiazol-2-yl)-4,5-dihydroisoxazol-3-yl]-1H-indazole (Compound No. 7)

1-Cyclopentyl-3-ethyl-6-[5-methyl-5-(1,3,4-oxadiazol-2-yl)-4,5-dihydroisoxazol-3-yl]-1H-indazole (Compound No. 8), 3-(1-Cyclopentyl-1H-indazol-6-yl)-5-methyl-4,5-dihydroisoxazole-5-carbohydrazide (Compound No. 16), Methyl 3-(1-cyclopentyl-3-methyl-1H-indazol-6-yl)-5-methyl-4,5-dihydroisoxazole-5-carboxylate (Compound No. 41), Methyl 3-(1-cyclopentyl-3-methyl-1H-indazol-6-yl)-5-(2-methoxy-2-oxoethyl)-4,5-dihydroisoxazole-5-carboxylate (Compound No. 44), Methyl 3-(1-cyclopentyl-3-ethyl-1H-indazol-6-yl)-5-methyl-4,5-dihydroisoxazole-5-carboxylate (Compound No. 46), Methyl 3-(1-cyclopentyl-3-ethyl-1H-indazol-6-yl)-5-(2-methoxy-2-oxoethyl)-4,5-dihydroisoxazole-5-carboxylate (Compound No. 49), 3-(1-Cyclopentyl-3-methyl-1H-indazol-6-yl)-N,5-dimethyl-4,5-dihydroisoxazole-5-carboxamide (Compound No. 51), 3-(1-Cyclopentyl-3-methyl-1H-indazol-6-yl)-5-methyl-N-propyl-4,5-dihydroisoxazole-5-carboxamide (Compound No. 52), 3-(1-Cyclopentyl-3-methyl-1H-indazol-6-yl)-N-cyclopropyl-5-methyl-4,5-dihydroisoxazole-5-carboxamide (Compound No. 53), 3-(1-Cyclopentyl-3-methyl-1H-indazol-6-yl)-N-methyl-5-[2-(methylamino)-2-oxoethyl]-4,5-dihydroisoxazole-5-carboxamide (Compound No. 54), 3-(1-Cyclopentyl-3-methyl-1H-indazol-6-yl)-5-[2-oxo-2-(propylamino)ethyl]-N-propyl-4,5-dihydroisoxazole-5-carboxamide (Compound No. 55), 3-(1-Cyclopentyl-3-methyl-1H-indazol-6-yl)-N-cyclopropyl-5-[2-(cyclopropylamino)-2-oxoethyl]-4,5-dihydroisoxazole-5-carboxamide (Compound No. 56), 3-(1-Cyclopentyl-3-ethyl-1H-indazol-6-yl)-N,5-dimethyl-4,5-dihydroisoxazole-5-carboxamide (Compound No. 57), 2-[3-(1-Cyclopentyl-3-ethyl-1H-indazol-6-yl)-5-methyl-4,5-dihydroisoxazol-5-yl]-N-propylacetamide (Compound No. 58), 3-(1-Cyclopentyl-3-ethyl-1H-indazol-6-yl)-N-cyclopropyl-5-methyl-4,5-dihydroisoxazole-5-carboxamide (Compound No. 59), 3-(1-Cyclopentyl-3-ethyl-1H-indazol-6-yl)-N-methyl-5-[2-(methylamino)-2-oxoethyl]-4,5-dihydroisoxazole-5-carboxamide (Compound No. 60), 3-(1-Cyclopentyl-3-ethyl-1H-indazol-6-yl)-5-[2-oxo-2-(propylamino)ethyl]-N-propyl-4,5-dihydroisoxazole-5-carboxamide (Compound No. 61), 3-(1-Cyclopentyl-3-ethyl-1H-indazol-6-yl)-N-cyclopropyl-5-[2-(cyclopropylamino)-2-oxoethyl]-4,5-dihydroisoxazole-5-carboxamide (Compound No. 62), Methyl 3-(3-ethyl-1-methyl-1H-indazol-6-yl)-5-(2-methoxy-2-oxoethyl)-4,5-dihydroisoxazole-5-carboxylate (Compound No. 63), Methyl 3-(1,3-dimethyl-1H-indazol-6-yl)-5-(2-methoxy-2-oxoethyl)-4,5-dihydroisoxazole-5-carboxylate (Compound No. 64), Methyl 3-(1-cyclopentyl-1H-indazol-6-yl)-5-methyl-4,5-dihydroisoxazole-5-carboxylate (Compound No. 65), Methyl 3-(1-cyclopentyl-1H-indazol-6-yl)-5-(2-methoxy-2-oxoethyl)-4,5-dihydroisoxazole-5-carboxylate (Compound No. 66), and 3-(1-Cyclopentyl-3-ethyl-1H-indazol-5-yl)-5-methyl-4,5-dihydroisoxazole-5-carbonitrile (Compound No. 67).

Scheme II

Formula X

Formula XI

Formula XII

The compounds of Formula XI and XII can be prepared by, for example, procedures as depicted in Scheme II. Thus a compound of Formula X (wherein $R_1$ and $R_2$ are the same as defined earlier) can be reacted with hydroxylamine hydrochloride to give a compound of Formula XI, which can be reacted with a compound of Formula $R^1COOH$ (wherein $R^1$ is aryl, cycloalkyl or heteroaryl) to give a compound of Formula XII.

The compound of Formula X can be reacted with hydroxylamine hydrochloride to give a compound of Formula XI in an organic solvent, for example, ethanol, methanol, propanol or isopropyl alcohol, in the presence of a base, for example, potassium carbonate, sodium carbonate or lithium carbonate.

The compound of Formula XI can be reacted with a compound of Formula $R^1COOH$ to give a compound of Formula XII in an organic solvent, for example, dimethylformamide, tetrahydrofuran, diethylether or dioxane, in the presence of a base, for example N-methylmorpholine, pyridine, diisopropylethylamine, 1,8-diazabicyclo[5,4,0]-undec-7-ene or 1,4-diazabicyclo[2,2,2]octane, with a coupling agent, for example, 1-(3-dimethylaminopropyl)-3-ethylcarbodiimide hydrochloride (EDCI.HCl) or 1,8-diazabicyclo[5.4.0]undec-7-ene (DBU).

Particular illustrative compounds which can be prepared following Scheme II include:

3-(1-Cyclopentyl-3-ethyl-1H-indazol-6-yl)-N'-hydroxy-5-methyl-4,5-dihydroisoxazole-5-carboximidamide (Compound No. 9), 1-Cyclopentyl-6-{5-[5-(3,5-dimethoxyphenyl)-1,2,4-oxadiazol-3-yl]-5-methyl-4,5-dihydroisoxazol-3-yl}-3-ethyl-1H-indazole (Compound No. 10), 6-{5-[5-(4-Chlorophenyl)-1,2,4-oxadiazol-3-yl]-5-methyl-4,5-dihydroisoxazol-3-yl}-1-cyclopentyl-3-ethyl-1H-indazole (Compound No. 11), 1-Cyclopentyl-3-ethyl-6-[5-methyl-5-(5-pyridin-3-yl-1,2,4-oxadiazol-3-yl)-4,5-dihydroisoxazol-3-yl]-1H-indazole (Compound No. 12), 1-Cyclopentyl-3-methyl-6-[5-methyl-5-(5-pyridin-4-yl-1,2,4-oxadiazol-3-yl)-4,5-dihydroisoxazol-3-yl]-1H-indazole (Compound No. 40), and 1-Cyclopentyl-6-{5-[5-(2,6-difluorophenyl)-1,2,4-oxadiazol-3-yl]-5-methyl-4,5-dihydroisoxazol-3-yl}-3-ethyl-1H-indazole (Compound No. 68).

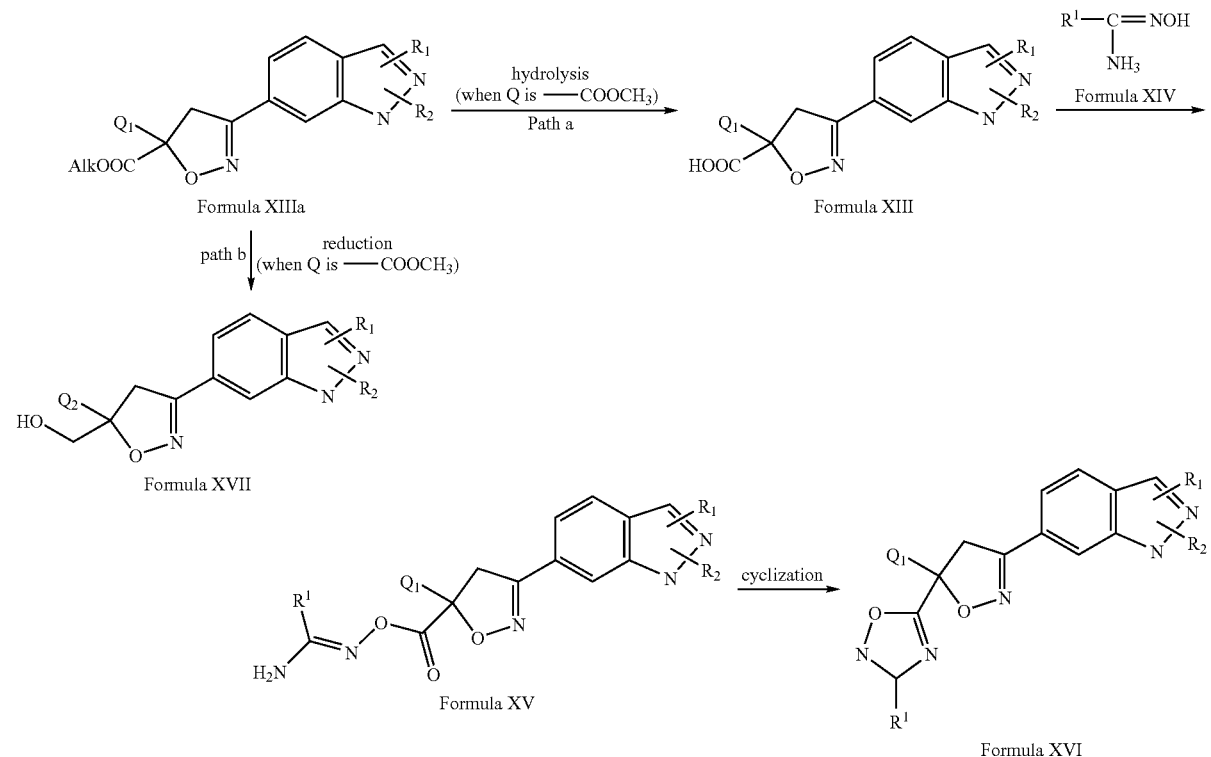

Scheme III

1-Cyclopentyl-3-ethyl-6-{5-[5-(4-fluorophenyl)-1,2,4-oxadiazol-3-yl]-5-methyl-4,5-dihydroisoxazol-3-yl}-1H-indazole (Compound No. 13), 1-Cyclopentyl-6-{5-[5-(3,4-difluorophenyl)-1,2,4-oxadiazol-3-yl]-5-methyl-4,5-dihydroisoxazol-3-yl}-3-ethyl-1H-indazole (Compound No. 14), 1-Cyclopentyl-6-{5-[5-(3,4-dimethoxyphenyl)-1,2,4-oxadiazol-3-yl]-5-methyl-4,5-dihydroisoxazol-3-yl}-3-ethyl-1H-indazole (Compound No. 15), 1-Cyclopentyl-6-{5-[5-(3,5-difluorophenyl)-1,2,4-oxadiazol-3-yl]-5-methyl-4,5-dihydroisoxazol-3-yl}-3-methyl-1H-indazole (Compound No. 35), 1-Cyclopentyl-6-{5-[5-(3,5-dimethoxyphenyl)-1,2,4-oxadiazol-3-yl]-5-methyl-4,5-dihydroisoxazol-3-yl}-3-methyl-1H-indazole, 1-Cyclopentyl-6-{5-[5-(4-fluorophenyl)-1,2,4-oxadiazol-3-yl]-5-methyl-4,5-dihydroisoxazol-3-yl}-3-methyl-1H-indazole (Compound No. 37), 6-{5-[5-(4-Chlorophenyl)-1,2,4-oxadiazol-3-yl]-5-methyl-4,5-dihydroisoxazol-3-yl}-1-cyclopentyl-3-methyl-1H-indazole (Compound No. 38), 1-Cyclopentyl-6-{5-[5-(2-fluorophenyl)-1,2,4-oxadiazol-3-yl]-5-methyl-4,5-dihydroisoxazol-3-yl}-3-methyl-1H-indazole (Compound No. 39), The compounds of Formula XIII, XVI and XVII can be prepared, for example, by following procedures as depicted in Scheme III. Thus, a compound of Formula XIIIa (wherein Alk is alkyl; Q=CH$_3$, —CH$_2$CO$_2$CH$_3$) can undergo hydrolysis (path a) to give a compound of Formula XIII (where R$_1$ and R$_2$ are the same as depicted earlier; Q$_1$=CH$_3$, —CH$_2$CO$_2$H), which can be reacted with a compound of Formula XIV (wherein R$^1$ is the same as defined earlier) to give a compound of Formula XV, which can undergo cyclisation to give a compound of Formula XVI. The compound of Formula XIIIa can undergo reduction (path b) to give a compound of Formula XVII (Q$_2$=CH$_3$, —CH$_2$CH$_2$OH).

The hydrolysis of a compound of Formula XIIIa to give a compound of Formula XIII can be carried out in an organic solvent, for example, tetrahydrofuran, dimethylformamide, diethylether or dioxane, in the presence of a base, for example, lithium hydroxide, potassium hydroxide or sodium hydroxide.

The reaction of a compound of Formula XIII with a compound of Formula XIV to give a compound of Formula XV can be carried out in an organic solvent, for example, dimethylformamide, tetrahydrofuran, diethylether or dioxane, in the presence of a base for example, N-methylmorpholine, diisopropylethylamine, pyridine or triethylamine, with a condensing agent, for example 1-(3-dimethylaminopropyl)-3-ethylcarbodiimide hydrochloride (EDCI.HCl) or dicyclohexylcarbodiimide (DCC).

The compound of Formula XV can undergo ring cyclisation to give a compound of Formula XVI in an organic solvent, for example, ethanol, methanol, propanol or isopropylalcohol, in the presence of buffer, for example, sodium acetate or potassium acetate or ammonium formate.

The reduction of a compound of Formula XIIIa to give a compound of Formula XVII can be carried out in an organic solvent, for example, tetrahydrofuran, dimethylformamide, diethylether or dioxane, with reducing agent, for example, sodium borohydride or sodium triacetoxyborohydride, in the presence of protic solvent, for example, methanol, ethanol or isopropyl alcohol.

Some particular illustrative the compounds which may be prepared following Scheme III include:

6-{5-[3-(2-Chlorophenyl)-1,2,4-oxadiazol-5-yl]-5-methyl-4,5-dihydroisoxazol-3-yl}-1-cyclopentyl-3-methyl-1H-indazole (Compound No. 17), 1-Cyclopentyl-6-{5-[3-(2,4-difluorophenyl)-1,2,4-oxadiazol-5-yl]-5-methyl-4,5-dihydroisoxazol-3-yl}-3-methyl-1H-indazole (Compound No. 18), 1-Cyclopentyl-6-{5-[3-(2,3-difluorophenyl)-1,2,4-oxadiazol-5-yl]-5-methyl-4,5-dihydroisoxazol-3-yl}-3-methyl-1H-indazole (Compound No. 19), 1-Cyclopentyl-6-{5-[3-(2,4-dimethoxyphenyl)-1,2,4-oxadiazol-5-yl]-5-methyl-4,5-dihydroisoxazol-3-yl}-3-methyl-1H-indazole (Compound No. 20), 1-Cyclopentyl-6-{5-[3-(2,5-dimethoxyphenyl)-1,2,4-oxadiazol-5-yl]-5-methyl-4,5-dihydroisoxazol-3-yl}-3-methyl-1H-indazole (Compound No. 21), 1-Cyclopentyl-6-{5-[3-(2,5-dichlorophenyl)-1,2,4-oxadiazol-5-yl]-5-methyl-4,5-dihydroisoxazol-3-yl}-3-methyl-1H-indazole (Compound No. 22), 1-Cyclopentyl-6-{5-[3-(2,5-difluorophenyl)-1,2,4-oxadiazol-5-yl]-5-methyl-4,5-dihydroisoxazol-3-yl}-3-methyl-1H-indazole (Compound No. 23), 1-Cyclopentyl-6-{5-[3-(3,4-difluorophenyl)-1,2,4-oxadiazol-5-yl]-5-methyl-4,5-dihydroisoxazol-3-yl}-3-methyl-1H-indazole (Compound No. 24), 1-Cyclopentyl-6-{5-[3-(2,3-dimethoxyphenyl)-1,2,4-oxadiazol-5-yl]-5-methyl-4,5-dihydroisoxazol-3-yl}-3-methyl-1H-indazole (Compound No. 25), 6-{5-[3-(2-Chlorophenyl)-1,2,4-oxadiazol-5-yl]-5-methyl-4,5-dihydroisoxazol-3-yl}-1-cyclopentyl-3-ethyl-1H-indazole (Compound No. 26), 1-Cyclopentyl-6-{5-[3-(2,4-difluorophenyl)-1,2,4-oxadiazol-5-yl]-5-methyl-4,5-dihydroisoxazol-3-yl}-3-ethyl-1H-indazole (Compound No. 27), 1-Cyclopentyl-6-{5-[3-(2,3-difluorophenyl)-1,2,4-oxadiazol-5-yl]-5-methyl-4,5-dihydroisoxazol-3-yl}-3-ethyl-1H-indazole (Compound No. 28), 1-Cyclopentyl-6-{5-[3-(2,4-dimethoxyphenyl)-1,2,4-oxadiazol-5-yl]-5-methyl-4,5-dihydroisoxazol-3-yl}-3-ethyl-1H-indazole (Compound No. 29), 1-Cyclopentyl-6-{5-[3-(2,5-dimethoxyphenyl)-1,2,4-oxadiazol-5-yl]-5-methyl-4,5-dihydroisoxazol-3-yl}-3-ethyl-1H-indazole (Compound No. 30), 1-Cyclopentyl-6-{5-[3-(2,5-dichlorophenyl)-1,2,4-oxadiazol-5-yl]-5-methyl-4,5-dihydroisoxazol-3-yl}-3-ethyl-1H-indazole (Compound No. 31), 1-Cyclopentyl-6-{5-[3-(2,5-difluorophenyl)-1,2,4-oxadiazol-5-yl]-5-methyl-4,5-dihydroisoxazol-3-yl}-3-ethyl-1H-indazole (Compound No. 32), 1-Cyclopentyl-6-{5-[3-(3,4-difluorophenyl)-1,2,4-oxadiazol-5-yl]-5-methyl-4,5-dihydroisoxazol-3-yl}-3-ethyl-1H-indazole (Compound No. 33), 1-Cyclopentyl-6-{5-[3-(3,4-difluorophenyl)-1,2,4-oxadiazol-5-yl]-5-methyl-4,5-dihydroisoxazol-3-yl}-3-ethyl-1H-indazole (Compound No. 34), 3-(1-Cyclopentyl-3-methyl-1H-indazol-6-yl)-5-methyl-4,5-dihydroisoxazole-5-carboxylic acid (Compound No. 42),

[3-(1-Cyclopentyl-3-methyl-1H-indazol-6-yl)-5-methyl-4,5-dihydroisoxazol-5-yl]methanol (Compound No. 43), 5-(Carboxymethyl)-3-(1-cyclopentyl-3-methyl-1H-indazol-6-yl)-4,5-dihydroisoxazole-5-carboxylic acid (Compound No. 45), 3-(1-Cyclopentyl-3-ethyl-1H-indazol-6-yl)-5-methyl-4,5-dihydroisoxazole-5-carboxylic acid (Compound No. 47),

[3-(1-Cyclopentyl-3-ethyl-1H-indazol-6-yl)-5-methyl-4,5-dihydroisoxazol-5-yl]methanol (Compound No. 48), 5-(Carboxymethyl)-3-(1-cyclopentyl-3-ethyl-1H-indazol-6-yl)-4,5-dihydroisoxazole-5-carboxylic acid (Compound No. 50), and their pharmaceutically acceptable salts, pharmaceutically acceptable solvates, stereoisomers or polymorphs.

In the above schemes, where specific bases, solvents, condensing agents, etc. are mentioned, it is to be understood that other acids, bases, solvents, condensing agents, hydrolyzing agents, etc, known to those skilled in an art may also be used. Similarly, the reaction temperature and duration of the reactions may be adjusted according to desired needs.

Where desired, the compounds of Formula Ia and/or their pharmaceutically acceptable salts, pharmaceutically acceptable solvates, stereoisomers, tautomers, racemates, prodrugs, metabolites, polymorphs or N-oxides may be advantageously used in combination with one or more other therapeutic agents. Examples of other therapeutic agents, which may be used in combination with compounds of Formula Ia of this invention and/or their pharmaceutically acceptable salts, pharmaceutically acceptable solvates, stereoisomers, tautomers, racemates, prodrugs, metabolites, polymorphs or N-oxides include corticosteroids, beta agonists, leukotriene antagonists, 5-lipoxygenase inhibitors, chemokine inhibitors and muscarinic receptor antagonists.

Because of their valuable pharmacological properties, the compounds described herein may be administered to an animal for treatment orally, or by a parenteral route. The pharmaceutical compositions described herein can be produced and administered in dosage units, each unit containing a certain amount of at least one compound described herein and/or at least one physiologically acceptable addition salt thereof. The dosage may be varied over extremely wide limits, as the compounds are effective at low dosage levels and relatively free of toxicity. The compounds may be administered in the low micromolar concentration, which is therapeutically effective, and the dosage may be increased as desired up to the maximum dosage tolerated by the patient.

The compounds described herein can be produced and formulated as their racemic mixtures, enantiomers, diastereomers, rotamers, N-oxides, polymorphs, solvates and pharmaceutically acceptable salts, as well as the active metabolites. Pharmaceutical compositions comprising the molecules of Formula Ia or metabolites, enantiomers, diastereomers, N-oxides, polymorphs, solvates or pharmaceutically acceptable salts thereof, in combination with pharmaceutically acceptable carrier and optionally included excipient can also be produced.

The examples mentioned below demonstrate general synthetic procedures, as well as specific preparations of particular compounds. The examples are provided to illustrate the details of the invention and should not be constrained to limit the scope of the present invention.

EXAMPLES

Synthesis of 6-bromo-1-cyclopentyl-1H-indazole, 6-bromo-1-cyclopentyl-3-methyl-1H-indazole and 6-bromo-1-cyclopentyl-3-ethyl-1H-indazole The title compounds were prepared following the procedure as described in U.S. Pat. No. 6,262,040 or Synthesis, 1999, 4, 588-592)

Example 1

3-(1-cyclopentyl-1H-indazol-6-yl)-5-methyl-4,5-dihydroisoxazole-5-carbonitrile (Compound No. 1)

Step a: 1-Cyclopentyl-1H-indazole-6-carboxaldehyde

A solution of the compound 6-bromo-1-cyclopentyl-1H-indazole (1.19 g, 4.15 mmol) in dry tetrahydrofuran (10 ml) was stirred at −78° C. for 15 minutes followed by the addition of butyl lithium (0.532 g, 8.3 mmol). The reaction mixture was again stirred for 30 minutes at −78° C. followed by the dropwise addition of dimethylformamide (1.212 g, 16.6 mmol). The reaction mixture was stirred for 30 minutes at the same temperature followed by stirring it at room temperature for 1 hour. The reaction mixture was quenched with hydrochloric acid (1N) and extracted the compound with ethyl acetate and water. The organic layer was collected, washed with brine and dried over anhydrous sodium sulphate. The mixture was filtered and concentrated under reduced pressure. The residue thus obtained was purified by column chromatography to furnish the title compound. Yield: 465 mg.

Mass (m/z): 215 ($M^+$+1). $^1$H NMR (CDCl$_3$): δ 10.07 (1H, s), 8.23 (1H, s), 8.03 (1H, s), 7.7 (1H, d), 7.62 (1H, d), 5.00 (1H, m), 2.3-1.2 (m, 8H).

Step b: 1-Cyclopentyl-1H-indazole-6-carboxaldehyde oxime

To a compound obtained from step a above (240 mg, 1.121 mmol) was added hydroxylamine hydrochloride (311.7 mg, 4.48 mmol) and sodium acetate (367 mg, 4.48 mmol) and ethanol (10 ml). The reaction mixture was stirred for 18 hours. The solvent was evaporated under reduced pressure and extracted the compound with ethyl acetate. The organic layer was collected, dried over anhydrous sodium sulphate, filtered and concentrated under reduced pressure. The residue thus obtained was purified by column chromatography using ethyl acetate in hexane solvent mixture as eluent to furnish the title compound. Yield: 260 mg.

Mass (m/z): 230.13 ($M^+$+1). $^1$H NMR (CDCl$_3$): δ 8.28 (s, 1H), 7.99 (s, 1H), 7.71-7.70 (d, 1H), 7.61 (s, 1H), 7.45-7.42 (dd, 1H), 5.05-4.98 (m, 1H), 2.2-1.75 (m, 8H).

Step c: 3-(1-Cyclopentyl-1H-indazol-6-yl)-5-methyl-4,5-dihydroisoxazole-5-carbonitrile To a mixture of compound obtained from step b above (50 mg, 0.218 mmol) and methylacrylonitrile (29.3 mg, 0.436 mmol) was added tetrahydrofuran (5 ml) and stirred the reaction mixture for 10 minutes at room temperature. To the resulting reaction mixture was added sodium hypochlorite (3 ml) with vigorous stirring, which was continued for 15 hours. The solvent was evaporated under reduced pressure and extracted the compound with ethyl acetate. The organic layer was separated, dried over anhydrous sodium sulphate and concentrated under reduced pressure to furnish the title compound. The residue thus obtained was purified by column chromatography using ethylacetate in hexane solvent mixture as eluent to furnish the title compound. Yield: 65 mg.

Mass (m/z): 295.10 ($M^+$+1).
$^1$H NMR (CDCl$_3$): δ 8.02 (1H, s), 7.77 (2H, dd), 7.45 (1H, d), 5.05 (1H, m), 3.99 (1H, d), 3.55 (1H, d), 2.22 (3H, m), 2.05-1.57 (8H, m).

The following compounds were prepared analogously,
3-(1-Cyclopentyl-3-methyl-1H-indazol-6-yl)-5-methyl-4,5-dihydroisoxazole-5-carbonitrile (Compound No. 2)
Mass (m/z): 309.30 ($M^+$+1).
3-(1-Cyclopentyl-3-ethyl-1H-indazol-6-yl)-5-methyl-4,5-dihydroisoxazole-5-carbonitrile (Compound No. 3)
Mass (m/z): 323.30 ($M^+$+1).
Methyl 3-(1-cyclopentyl-3-methyl-1H-indazol-6-yl)-5-methyl-4,5-dihydroisoxazole-5-carboxylate (Compound No. 41)
Mass (m/z): 342 ($M^+$+1).
Methyl 3-(1-cyclopentyl-3-methyl-1H-indazol-6-yl)-5-(2-methoxy-2-oxoethyl-4,5-dihydroisoxazole-5-carboxylate (Compound No. 44)
Mass (m/z): 400 ($M^+$+1).
Methyl 3-(1-cyclopentyl-3-ethyl-1H-indazol-6-yl)-5-methyl-4,5-dihydroisoxazole-5-carboxylate (Compound No. 46)
Mass (m/z): 356.1 ($M^+$+1).
Methyl 3-(1-cyclopentyl-3-ethyl-1H-indazol-6-yl)-5-(2-methoxy-2-oxoethyl)-4,5-dihydroisoxazole-5-carboxylate (Compound No. 49)
Mass (m/z): 414.1 ($M^+$+1).
Methyl 3-(3-ethyl-1-methyl-1H-indazol-6-yl)-5-(2-methoxy-2-oxoethyl)-4,5-dihydroisoxazole-5-carboxylate (Compound No. 63)
Mass (m/z): 360.1 ($M^+$+1).
Methyl 3-(1,3-dimethyl-1H-indazol-6-yl)-5-(2-methoxy-2-oxoethyl)-4,5-dihydroisoxazole-5-carboxylate (Compound No. 64)
Mass (m/z): 346.1 ($M^+$+1).
Methyl 3-(1-cyclopentyl-1H-indazol-6-yl)-5-methyl-4,5-dihydroisoxazole-5-carboxylate (Compound No. 65)
Mass (1-m/z): 329.00 ($M^+$+1).
Methyl 3-(1-cyclopentyl-1H-indazol-6-yl)-5-(2-methoxy-2-oxoethyl)-4,5-dihydroisoxazole-5-carboxylate (Compound No. 66).
Mass (m/z): 386.1 ($M^+$+1).
3-(1-Cyclopentyl-3-ethyl-1H-indazol-5-yl)-5-methyl-4,5-dihydroisoxazole-5-carbonitrile (Compound No. 67).
Mass (m/z): 323.1 ($M^+$+1).

Scheme I, Formula VI, Path a

Example 2

Synthesis of 3-(1-cyclopentyl-1H-indazol-6-yl)-5-methyl-4,5-dihydroisoxazole-5-carbohydrazide (Compound No. 16)

To the compound no. 65 (122 mg, 0.317 mmol) was added hydrazine hydrate (117.16 mg, 2.3 mmol) and refluxed the reaction mixture for 4 hours at 80-85° C. The reaction mixture was extracted with ethyl acetate. The organic layer was separated, dried over anhydrous sodium sulphate, filtered and dried under reduced pressure to furnish the title compound. Yield: 85 mg.

The following compounds were prepared analogously,
3-(1-Cyclopentyl-3-methyl-1H-indazol-6-yl)-5-methyl-4,5-dihydroisoxazole-5-carbohydrazide (Compound No. 4)
3-(1-Cyclopentyl-3-ethyl-1H-indazol-6-yl)-5-methyl-4,5-dihydroisoxazole-5-carbohydrazide (Compound No. 5)

Example 3

Synthesis of 1-cyclopentyl-6-[5-methyl-5-(1,34-oxadiazol-2-yl)-4,5-dihydroisoxazol-3-yl]-1H-indazole (Compound No. 6)

To the compound no. 16 (85 mg, 0.259 mmol) was added triethyl orthoformate (0.275 g, 1.85 mmol) and stirred the reaction mixture for 3 hours at 120-125° C. Excess of triethyl orthoformate was evaporated under reduced pressure under inert atmosphere. Residual mixture was again stirred for 12 hours stirred for at 140-145° C. and subsequently extracted the compound with ethyl acetate. The organic extracts were collected, dried over anhydrous sodium sulphate, filtered and concentrated under reduced pressure. The residue thus obtained was purified by column chromatography using ethylacetate in hexane solvent mixture was eluent to furnish the title compound. Yield: 70 mg.

Mass (m/z): 338 (M$^+$+1). $^1$H NMR (CDCl$_3$): δ 8.46 (1H, s), 8.02 (1H, s), 7.76 (2H, d), 7.74 (1H, d), 5.03 (1H, m), 4.41 (1H, d), 3.61 (1H, d), 2.20-1.59 (8H, m), 1.37 (3H, s).

The following compound were prepared analogously,
1-Cyclopentyl-3-methyl-6-[5-methyl-5-(1,3,4-oxadiazol-2-yl)-4,5-dihydroisoxazol-3-yl]-1H-indazole (Compound No. 7)
Mass (m/z): 352.30 (M$^+$+1).
1-Cyclopentyl-3-ethyl-6-[5-methyl-5-(1,3,4-oxadiazol-2-yl)-4,5-dihydroisoxazol-3-yl]1H-indazole (Compound No. 8)
Mass (m/z): 366.30 (M$^+$+1).

Example 4

Synthesis of 3-(1-cyclopentyl-3-methyl-1H-indazol-6-yl)-N,5-dimethyl-4,5-dihydroisoxazole-5-carboxamide (Compound No. 51)

A solution of the Compound No. 41 (0.146 mmol) and methylamine (11.0 ml) was refluxed for 10 hours at 55-60° C. The mixture was cooled to room temperature and washed with hexane. The solid thus separated was diluted with chloroform and purified by preparative column chromatography using 10% methanol in dichloromethane to furnish the title compound. Yield: 0.024 g
$^1$H NMR (CDCl$_3$): δ 7.65 (1H, d), 7.56 (1H, s), 7.45 (1H, d), 6.93 (1H, b), 4.90 (1H, m), 3.97-3.93 (1H, dd), 3.35-3.31 (1H, dd), 2.85 (3H, d), 2.57 (3H, s), 2.16-1.71 (11H, m).

The following compound were prepared analogously,
3-(1-Cyclopentyl-3-methyl-1H-indazol-6-yl)-5-methyl-N-propyl-4,5-dihydroisoxazole-5-carboxamide (Compound No. 52)
Mass (m/z): 369.1 (M$^+$+1).
3-(1-Cyclopentyl-3-methyl-1H-indazol-6-yl)-N-cyclopropyl-5-methyl-4,5-dihydroisoxazole-5-carboxamide (Compound No. 53)
Mass (m/z): 367.1 (M$^+$+1).
3-(1-Cyclopentyl-3-methyl-1H-indazol-6-yl)-N-methyl-5-[2-(methylamino)-2-oxoethyl]-4,5-dihydroisoxazole-5-carboxamide (Compound No. 54)
$^1$H NMR (CDCl$_3$): δ 7.64 (1H, d), 7.54 (1H, s), 7.45 (1H, d), 6.97 (1H, b), 6.19 (1H, bs), 4.89 (1H, m), 3.84 (2H, s), 3.00-2.80 (5H, dd), 2.57 (3H, s), 2.17-1.73 (8H, m), 1.57 (3H, bs).
3-(1-Cyclopentyl-3-methyl-1H-indazol-6-yl)-5-[2-oxo-2-(propylamino-ethyl]-N-propyl-4,5-dihydroisoxazole-5-carboxamide (Compound No. 55)
Mass (m/z): 454.2 (M$^+$+1).
3-(1-Cyclopentyl-3-methyl-1H-indazol-6-yl)-N-cyclopropyl-5-[2-(cyclopropylamino)-2-oxoethyl]-4,5-dihydroisoxazole-5-carboxamide (Compound No. 56)
$^1$H NMR (CDCl$_3$): δ 7.65 (1H, d), 7.53 (1H, s), 7.46 (1H, d), 6.94 (1H, bs), 6.24 (1H, bs), 4.92 (1H, m), 3.82 (2H, s), 2.89 (2H, d), 2.80-2.60 (2H, m), 2.57 (3H, s), 2.16-1.73 (8H, m), 1.59 (3H, bs), 0.81-0.73 (4H, m), 0.56-0.50 (4H, m).
3-(1-Cyclopentyl-3-ethyl-1H-indazol-6-yl)-N,5-dimethyl-4,5-dihydroisoxazole-5-carboxamide (Compound No. 57)
Mass (m/z): 355.1 (M$^+$+1).
2-[3-(1-Cyclopentyl-3-ethyl-1H-indazol-6-yl)-5-methyl-4,5-dihydroisoxazol-5-yl]-N-propylacetamide (Compound No. 58)
Mass (m/z): 383.1 (M$^+$+1).
3-(1-Cyclopentyl-3-ethyl-1H-indazol-6-yl)-N-cyclopropyl-5-methyl-4,5-dihydroisoxazole-5-carboxamide (Compound No. 59)
Mass (m/z): 380.1 (M$^+$+1).
3-(1-Cyclopentyl-3-ethyl-1H-indazol-6-yl)-N-methyl-5-[2-(methylamino)-2-oxoethyl]-4,5-dihydroisoxazole-5-carboxamide (Compound No. 60)
Mass (m/z): 412.1 (M$^+$+1).
3-(1-Cyclopentyl-3-ethyl-1H-indazol-6-yl)-5-[2-oxo-2-(propylamino)ethyl]-N-propyl-4,5-dihydroisoxazole-5-carboxamide (Compound No. 61)
Mass (m/z): 468.2 (M$^+$+1).
3-(1-Cyclopentyl-3-ethyl-1H-indazol-6-yl)-N-cyclopropyl-5-[2-(cyclopropylamino)-2-oxoethyl]-4,5-dihydroisoxazole-5-carboxamide (Compound No. 62)
Mass (m/z): 464.1 (M$^+$+1).

Example 5

Synthesis of 3-(1-cyclopentyl-3-ethyl-1H-indazol-6-yl)-N'-hydroxy-5-methyl-4,5-dihydroisoxazole-5-carboximidamide (Compound No. 9)

To Compound No. 3 (1.5 g, 4.8 mmol) was added hydroxylamine hydrochloride (1.33 g, 19.2 mmol) and potassium carbonate (1.99 g, 14.4 mmol) followed by the addition of ethanol (15 ml) and refluxed the reaction mixture for 24 hours at 80-90° C. The solvent was evaporated under reduced pressure and extracted the product with ethyl acetate. The organic extracts were collected, dried over anhydrous sodium sulphate and filtered. The filtrate was concentrated under reduced pressure and the residue thus obtained was purified by column chromatography using ethyl acetate in hexane solvent mixture as eluent to furnish the title compound. Yield: 920 mg.

Mass (m/z): 356.3 (M$^+$+1).

Example 6

Synthesis of 1-cyclopentyl-6-{5-[5-(3,5-dimethoxyphenyl)-1,2,4-oxadiazol-3-yl]-5-methyl-4,5-dihydroisoxazol-3-yl}-3-ethyl-1H-indazole (Compound No. 10)

To a mixture of compound No. 9 (100 mg, 0.282 mmol) and 3,5-dimethoxybenzoic acid (56 mg, 0.309 mmol) was added dimethylformamide (5 ml) and cooled the reaction mixture to 0° C. To it was added hydroxybenzotriazole (38 mg, 0.282 mmol) and N-methylmorpholine (0.113 g, 1.128 mmol) followed by the addition 1-(3-dimethylamino propyl)-3-ethylcarbodiimide hydrochloride (0.108 g, 0.564 mmol). The resulting reaction mixture was stirred for 18 hours. It was diluted with water and extracted with ethyl acetate. The organic extracts were collected, dried over anhydrous sodium sulphate, filtered and concentrated under reduced pressure. To the residue thus obtained was added dimethylformamide (2 ml) and refluxed the reaction mixture for 20 hours. Dimethyl formamide was evaporated under reduced pressure and extracted the compound with ethyl acetate. The organic extracts were collected, dried over anhydrous sodium sulphate, filtered and dried under reduced pressure. The residue thus obtained was purified by preparative column chromatography to furnish the title compound. Yield: 70 mg.

Mass (m/z): 502.2 ($M^++1$). $^1H$ NMR (CDCl$_3$): δ 7.71 (2H, d), 7.50 (1H, d), 7.28 (4H, d), 4.95 (1H, m), 4.27 (1H, d), 3.86 (6H, s), 3.5 (1H, d), 2.97 (2H, q), 2.17 (3H, s), 2.01-1.73 (8H, m), 1.37 (3H, t).

The following compounds were prepared analogously,

6-{5-[5-(4-Chlorophenyl)-1,2,4-oxadiazol-3-yl]-5-methyl-4,5-dihydroisoxazol-3-yl}-1-cyclopentyl-3-ethyl-1H-indazole (Compound No. 11)
Mass (m/z): 476.2 ($M^++1$). m.p: 154-155° C.

1-Cyclopentyl-3-ethyl-6-[5-methyl-5-(5-pyridin-3-yl-1,2,4-oxadiazol-3-yl)-4,5-dihydroisoxazol-3-yl]-1H-indazole (Compound No. 12)
Mass (m/z): 443.10 ($M^++1$). m.p: 161-168° C.

1-Cyclopentyl-3-ethyl-6-{5-[5-(4-fluorophenyl)-1,2,4-oxadiazol-3-yl]-5-methyl-4,5-dihydroisoxazol-3-yl}-1H-indazole (Compound No. 13)
Mass (m/z): 460.10 ($M^++1$). m.p: 87-88° C.

1-Cyclopentyl-6-{5-[5-(3,4-difluorophenyl)-1,2,4-oxadiazol-3-yl]-5-methyl-4,5-dihydroisoxazol-3-yl}-3-ethyl-1H-indazole (Compound No. 14)
Mass (m/z): 478.1 ($M^++1$).

1-Cyclopentyl-6-{5-[5-(3,4-dimethoxyphenyl)-1,2,4-oxadiazol-3-yl]-5-methyl-4,5-dihydroisoxazol-3-yl}-3-ethyl-1H-indazole (Compound No. 15)
Mass (m/z): 502.2 ($M^++1$).

1-Cyclopentyl-6-{5-[5-(3,5-difluorophenyl)-1,2,4-oxadiazol-3-yl]-5-methyl-4,5-dihydroisoxazol-3-yl}-3-methyl-1H-indazole (Compound No. 35)
Mass (m/z): 464.1 ($M^++1$).

1-Cyclopentyl-6-{5-[5-(3,5-dimethoxyphenyl)-1,2,4-oxadiazol-3-yl]-5-methyl-4,5-dihydroisoxazol-3-yl}-3-methyl-1H-indazole (Compound No. 36)
Mass (m/z): 488.1 ($M^++1$).

1-Cyclopentyl-6-{5-[5-(4-fluorophenyl)-1,2,4-oxadiazol-3-yl]-5-methyl-4,5-dihydroisoxazol-3-yl}-3-methyl-1H-indazole (Compound No. 37)
Mass (m/z): 446.1 ($M^++1$).

6-{5-[5-(4-Chlorophenyl)-1,2,4-oxadiazol-3-yl]-5-methyl-4,5-dihydroisoxazol-3-yl}-1-cyclopentyl-3-methyl-1H-indazole (Compound No. 38)
Mass (m/z): 462 ($M^++1$).

1-Cyclopentyl-6-{5-[5-(2-fluorophenyl)-1,2,4-oxadiazol-3-yl]-5-methyl-4,5-dihydroisoxazol-3-yl}-3-methyl-1H-indazole (Compound No. 39)
Mass (m/z): 446.1 ($M^++1$).

1-Cyclopentyl-3-methyl-6-[5-methyl-5-(5-pyridin-4-yl-1,2,4-oxadiazol-3-yl)-4,5-dihydroisoxazol-3-yl]-1H-indazole (Compound No. 40)
Mass (m/z): 429 ($M^++1$).

1-Cyclopentyl-6-{5-[5-(2,6-difluorophenyl)-1,2,4-oxadiazol-3-yl]-5-methyl-4,5-dihydroisoxazol-3-yl}-3-ethyl-1H-indazole (Compound No. 68)
Mass (m/z): 478.1 ($M^++1$).

Example 7

Synthesis of 3-(1-cyclopentyl-3-ethyl-1H-indazol-6-yl)-5-methyl-4,5-dihydroisoxazole-5-carboxylic acid (Compound No. 47)

To a solution of compound No. 46 (0.050 g, 0.140 mmol) in tetrahydrofuran, lithium hydroxide (0.015 g, 0.352 mmol) was added and refluxed at 55-60° C. for overnight. The reaction mixture was cooled and water (15 ml) was added. The aqueous layer was washed with ethyl acetate (5 ml). The aqueous layer was acidified and extracted with ethyl acetate. The organic extracts were collected, dried over anhydrous sodium sulphate, filtered and dried under reduced pressure. The residue thus obtained was purified by preparative column chromatography to furnish the title compound. Yield: 0.025 g
Mass (m/z): 342 ($M^++1$).

Following compound were prepared analogously, 3-(1-Cyclopentyl-3-methyl-1H-indazol-6-yl)-5-methyl-4,5-dihydroisoxazole-5-carboxylic acid (Compound No. 42
Mass (m/z): 328 ($M^++1$).

5-(Carboxymethyl)-3-(1-cyclopentyl-3-methyl-1H-indazol-6-yl)-4,5-dihydroisoxazole-5-carboxylic acid (Compound No. 45)

5-(Carboxymethyl)-3-(1-cyclopentyl-3-ethyl-1H-indazol-6-yl)-4,5-dihydroisoxazole-5-carboxylic acid (Compound No. 50)
Mass (m/z): 386 ($M^++1$).

Example 8

Synthesis of 6-{5-[3-(2-chlorophenyl)-1,2,4-oxadiazol-5-yl]-5-methyl-4,5-dihydroisoxazol-3-yl}-1-cyclopentyl-3-ethyl-1H-indazole (Compound No. 26)

Step a: Synthesis of 2-chloro-N'-({[3-(1-cyclopentyl-3-ethyl-1H-indazol-6-yl)-5-methyl-4,5-dihydroisoxazol-5-yl]carbonyl}oxy)benzenecarboximidamide A solution of the Compound No. 47 (0.100 g, 0.294 mmol) and 2-chloro-N-hydroxy benzamidine (0.055 g, 0.323 mmol) in dimethylformamide (5 ml) was cooled at 0° C. and stirred for 15 minutes followed by the addition of hydroxybenzotriazole (0.040 g, 0.294 mmol) and N-methylmorpholine (0.0118 g, 1.168 mmol) at the same temperature. The resulting reaction mixture was stirred for 1 hour followed by the addition of 1-(3-dimethylaminopropyl)-3-ethylcarbodiimide hydrochloride (0.113 g, 0.589 mmol). The reaction mixture was stirred for 18 hours at room temperature. The mixture was extracted with ethylacetate and water. The organic layer was separated, washed with water and brine, dried over anhydrous sodium sulphate, filtered and concentrated under reduced pressure to furnish the title compound. Yield: 115 mg.

Step b: 6-{5-[3-(2-Chlorophenyl)-1,2,4-oxadiazol-5-yl]-5-methyl-4,5-dihydroisoxazol-3-yl}-1-cyclopentyl-3-ethyl-1H-indazole (Compound No. 26)

To a solution of the compound obtained from step a above (0.110 g, 0.222 mmol) in ethanol (6 ml), water (1.0 mL) and sodium acetate (0.036 g, 0.444 mmol) were added. The reaction mixture was refluxed at 90° C. for 16 hours. Solvent was evaporated under reduced pressure and the residue thus obtained was diluted with water. The solid thus separated was washed with water and dried under reduced pressure.

Yield: 0.030 g. Mass (m/z): 476 ($M^+$+1).

The compounds described below were prepared analogously, 6-{5-[3-(2-Chlorophenyl)-1,2,4-oxadiazol-5-yl]-5-methyl-4,5-dihydroisoxazol-3-yl}-1-cyclopentyl-3-methyl-1H-indazole (Compound No. 17)
Mass (m/z): 462 ($M^+$+1).
1-Cyclopentyl-6-{5-[3-(2,4-difluorophenyl)-1,2,4-oxadiazol-5-yl]-5-methyl-4,5-dihydroisoxazol-3-yl}-3-methyl-1H-indazole (Compound No. 18)
Mass (m/z): 464 ($M^+$+1).
1-Cyclopentyl-6-{5-[3-(2,3-difluorophenyl)-1,2,4-oxadiazol-5-yl]-5-methyl-4,5-dihydroisoxazol-3-yl}-3-methyl-1H-indazole (Compound No. 19)
Mass (m/z): 464 ($M^+$+1).
1-Cyclopentyl-6-{5-[3-(2,4-dimethoxyphenyl)-1,2,4-oxadiazol-5-yl]-5-methyl-4,5-dihydroisoxazol-3-yl}-3-methyl-1H-indazole (Compound No. 20)
Mass (m/z): 488 ($M^+$+1).
1-Cyclopentyl-6-{5-[3-(2,5-dimethoxyphenyl)-1,2,4-oxadiazol-5-yl]-5-methyl-4,5-dihydroisoxazol-3-yl}-3-methyl-1H-indazole (Compound No. 21)
Mass (m/z): 488 ($M^+$+1).
1-Cyclopentyl-6-{5-[3-(2,5-dichlorophenyl)-1,2,4-oxadiazol-5-yl]-5-methyl-4,5-dihydroisoxazol-3-yl}-3-methyl-1H-indazole (Compound No. 22)
Mass (m/z): 496 ($M^+$+1).
1-Cyclopentyl-6-{5-[3-(2,5-difluorophenyl)-1,2,4-oxadiazol-5-yl]-5-methyl-4,5-dihydroisoxazol-3-yl}-3-methyl-1H-indazole (Compound No. 23)
Mass (m/z): 464 ($M^+$+1).
1-Cyclopentyl-6-{5-[3-(3,4-difluorophenyl)-1,2,4-oxadiazol-5-yl]-5-methyl-4,5-dihydroisoxazol-3-yl}-3-methyl-1H-indazole (Compound No. 24)
Mass (m/z): 464 ($M^+$+1).
1-Cyclopentyl-6-{5-[3-(2,3-dimethoxyphenyl-1,2,4-oxadiazol-5-yl]-5-methyl-4,5-dihydroisoxazol-3-yl}-3-methyl-1H-indazole (Compound No. 25)
Mass (m/z): 488 ($M^+$+1).
1-Cyclopentyl-6-{5-[3-(2,4-difluorophenyl)-1,2,4-oxadiazol-5-yl]-5-methyl-4,5-dihydroisoxazol-3-yl}-3-ethyl-1H-indazole (Compound No. 27)
Mass (m/z): 478.1 ($M^+$+1).
1-Cyclopentyl-6-{5-[3-(2,3-difluorophenyl)-1,2,4-oxadiazol-5-yl]-5-methyl-4,5-dihydroisoxazol-3-yl}-3-ethyl-1H-indazole (Compound No. 28)
Mass (m/z): 478.1 ($M^+$+1).
1-Cyclopentyl-6-{5-[3-(2,4-dimethoxyphenyl)-1,24-oxadiazol-5-yl]-5-methyl-4,5-dihydroisoxazol-3-yl}-3-ethyl-1H-indazole (Compound No. 29)
Mass (m/z): 502.1 ($M^+$+1).
1-Cyclopentyl-6-{5-[3-(2,5-dimethoxyphenyl)-1,2,4-oxadiazol-5-yl]-5-methyl-4,5-dihydroisoxazol-3-yl}-3-ethyl-1H-indazole (Compound No. 30)
Mass (m/z): 502 ($M^+$+1).
1-Cyclopentyl-6-{5-[3-(2,5-dichlorophenyl)-1,2,4-oxadiazol-5-yl]-5-methyl-4,5-dihydroisoxazol-3-yl}-3-ethyl-1H-indazole (Compound No. 31
Mass (m/z): 510 ($M^+$+1).
1-Cyclopentyl-6-{5-[3-(2,5-difluorophenyl)-1,2,4-oxadiazol-5-yl]-5-methyl-4,5-dihydroisoxazol-3-yl}-3-ethyl-1H-indazole (Compound No. 32)
Mass (m/z): 478.1 ($M^+$+1).
1-Cyclopentyl-6-{5-[3-(3,4-difluorophenyl)-1,2,4-oxadiazol-5-yl]-5-methyl-4,5-dihydroisoxazol-3-yl}-3-ethyl-1H-indazole (Compound No. 33)
Mass (m/z): 478.1 ($M^+$+1).
1-Cyclopentyl-6-{5-[3-(3,4-difluorophenyl)-1,2,4-oxadiazol-5-yl]-5-methyl-4,5-dihydroisoxazol-3-yl}-3-ethyl-1H-indazole (Compound No. 34)
Mass (m/z): 502.1 ($M^+$+1).

Example 8

Synthesis of [3-(1-cyclopentyl-3-ethyl-1H-indazol-6-yl)-5-methyl-4,5-dihydroisoxazol-5-yl]methanol (Compound No. 48)

To a solution of compound No. 46 (0.050 g, 0.140 mmol) in tetrahydrofuran, sodium borohydride (0.013, 0.352 mmol) were added at 0-5° C. The reaction mixture was stirred at room temperature for 6 h. Excess of sodium borohydride was quenched with saturated ammonium chloride and extracted with ethyl acetate. The organic layer was separated, washed with water and dried over anhydrous sodium sulphate, filtered and concentrated under reduced pressure to furnish the title compound. Yield: 0.024 g. Mass (m/z): 328.1 ($M^+$+1).

The following compound was prepared analogously,
[3-(1-Cyclopentyl-3-methyl-1H-indazol-6-yl)-5-methyl-4,5-dihydroisoxazol-5-yl]methanol (Compound No. 43)
Mass (m/z): 314 ($M^+$+1).

Efficacy of Compounds as PDE IV Inhibitors

PDE-IV Enzyme Assay:

The efficacy of compounds as PDE-4 inhibitor was determined by an enzyme assay (Burnouf et al; J. Med. Chem. 2000, 43:4850-4867). The PDE-4 enzyme source used was U937 cell cytosolic fraction prepared by sonication. The enzyme reaction was carried out, with the cytosolic fraction as the enzyme source, in the presence of cAMP (1 µM) at 30° C. in the presence or absence of NCE for 45-60 min. An aliquot of this reaction mixture was taken further for the ELISA assay to determine level of cAMP in the sample. The concentration of the cAMP in the sample directly correlates with the degree of PDE-4 enzyme inhibition. Results were expressed as percent control and the $IC_{50}$ values of compounds 1-3, 6-8, 10-15 and 17-36 were found to be in the range of between about 0.1 nm to about 10,000 nM, for example, from about 0.1 nM to about 1000 nM, for example, from about 0.1 nM to about 500 nM, for example, from about 0.1 nM to about 200 nM, or for example, from about 0.1 nM to about 25 nM.

The standard compound, (n=7) rolipram, had activity of about 460 nM in the PDE-4 assay.

Cell based Assay for TNF-α Release

Method of Isolation of Human Peripheral Blood Mononuclear Cells:

Human whole blood was collected in vacutainer tubes containing heparin or EDTA as an anti coagulant. The blood was diluted (1:1) in sterile phosphate buffered saline and 10 ml. was carefully layered over 5 ml Ficoll Hypaque gradient (density 1.077 g/ml) in a 15 ml conical centrifuge tube. The sample was centrifuged at 3000 rpm for 25 minutes in a swing-out rotor at room temperature. After centrifugation, interface of cells were collected, diluted at least 1:5 with PBS and washed three times by centrifugation at 2500 rpm for 10 minutes at room temperature. The cells were resuspended in serum free RPMI 1640 medium at a concentration of 2 million cells/ml. Alternatively whole blood was used.

LPS Stimulation of Human PBMNC's:

PBMN cells (0.1 ml; 2 million/ml) were co-incubated with 20 μl of compound (final DMSO concentration of 0.2%) for 10 min in a flat bottom 96 well microtiter plate. Compounds were dissolved in DMSO initially and diluted in medium for a final concentration of 0.2% DMSO. LPS (1 μg/ml, final concentration) was then added at a volume of 10 μl per well. After 30 min, 20 μl of fetal calf serum (final concentration of 10%) was added to each well. Cultures were incubated overnight at 37° C. in an atmosphere of 5% $CO_2$ and 95% air. Supernatant were then removed and tested by ELISA for TNF-α release using a commercial kit (e.g. BD Biosciences). For whole blood, the plasma samples were diluted 1:20 for ELISA. The level of TNF-α in treated wells was compared with the vehicle treated controls and inhibitory potency of compound was expressed as $IC_{50}$ values calculated by using Graph pad prism.

Compounds 2, 3, 23, 31 and 32 were tested by the TNF assay, giving $IC_{50}$ from about 4.2 μM to about 10 μM, or from about 4.2 μM to about 8.0 μM, or from 4.2 μM to about 4.9 μM, as compared to the standard (M=6) rolipram (1.2 μM).

We claim:
1. A compound having the structure of Formula Ia

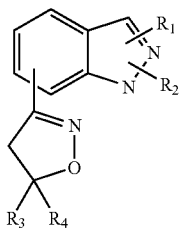

Formula Ia its pharmaceutically acceptable salts, enantiomers, or diastereomers wherein $R_1$ and $R_2$ are independently selected from hydrogen, alkyl, alkenyl, alkynyl, aryl, aralkyl, heteroaryl, heterocyclyl, cycloalkyl, alkoxy, halogen or —OH;

$R_3$ is alkyl, alkenyl, alkynyl, cycloalkyl, carboxy, heteroaryl, heterocyclyl, aryl, heteroarylalkyl, heterocyclylalkyl, aralkyl or carboxyalkyl; and $R_4$ is cyano, cycloalkyl, aryl, heteroaryl, heterocyclyl, aralkyl, heteroarylalkyl, heterocyclylalkyl, —CONHNH$_2$, —C(=NOH)NH$_2$ or carboxyalkyl.

2. A compound selected from:
3-(1-Cyclopentyl-1H-indazol-6-yl)-5-methyl-4,5-dihydroisoxazole-5-carbonitrile (Compound No. 1),
3-(1-Cyclopentyl-3-methyl-1H-indazol-6-yl)-5-methyl-4,5-dihydroisoxazole-5-carbonitrile (Compound No. 2),
3-(1-Cyclopentyl-3-ethyl-1H-indazol-6-yl)-5-methyl-4,5-dihydroisoxazole-5-carbonitrile (Compound No. 3),
3-(1-Cyclopentyl-3-methyl-1H-indazol-6-yl)-5-methyl-4,5-dihydroisoxazole-5-carbohydrazide (Compound No. 4)
3-(1-Cyclopentyl-3-ethyl-1H-indazol-6-yl)-5-methyl-4,5-dihydroisoxazole-5-carbohydrazide (Compound No. 5)
1-Cyclopentyl-6-[5-methyl-5-(1,3,4-oxadiazol-2-yl)-4,5-dihydroisoxazol-3-yl]-1H-indazole (Compound No. 6)
1-Cyclopentyl-3-methyl-6-[5-methyl-5-(1,3,4-oxadiazol-2-yl)-4,5-dihydroisoxazol-3-yl]-1H-indazole (Compound No. 7)
1-Cyclopentyl-3-ethyl-6-[5-methyl-5-(1,3,4-oxadiazol-2-yl)-4,5-dihydroisoxazol-3-yl]-1H-indazole (Compound No. 8),
3-(1-Cyclopentyl-3-ethyl-1H-indazol-6-yl)-N'-hydroxy-5-methyl-4,5-dihydroisoxazole-5-carboximidamide (Compound No. 9),
1-Cyclopentyl-6-{5-[5-(3,5-dimethoxyphenyl)-1,2,4-oxadiazol-3-yl]-5-methyl-4,5-dihydroisoxazol-3-yl}-3-ethyl-1H-indazole (Compound No. 10),
6-{5-[5-(4-Chlorophenyl)-1,2,4-oxadiazol-3-yl]-5-methyl-4,5-dihydroisoxazol-3-yl}-1-cyclopentyl-3-ethyl-1H-indazole (Compound No. 11),
1-Cyclopentyl-3-ethyl-6-[5-methyl-5-(5-pyridin-3-yl-1,2,4-oxadiazol-3-yl)-4,5-dihydroisoxazol-3-yl]-1H-indazole (Compound No. 12),
1-Cyclopentyl-3-ethyl-6-{5-[5-(4-fluorophenyl)-1,2,4-oxadiazol-3-yl]-5-methyl-4,5-dihydroisoxazol-3-yl}-1H-indazole (Compound No. 13),
1-Cyclopentyl-6-{5-[5-(3,4-difluorophenyl)-1,2,4-oxadiazol-3-yl]-5-methyl-4,5-dihydroisoxazol-3-yl}-3-ethyl-1H-indazole (Compound No. 14),
1-Cyclopentyl-6-{5-[5-(3,4-dimethoxyphenyl)-1,2,4-oxadiazol-3-yl]-5-methyl-4,5-dihydroisoxazol-3-yl}-3-ethyl-1H-indazole (Compound No. 15),
3-(1-Cyclopentyl-1H-indazol-6-yl)-5-methyl-4,5-dihydroisoxazole-5-carbohydrazide (Compound No. 16),
6-{5-[3-(2-Chlorophenyl)-1,2,4-oxadiazol-5-yl]-5-methyl-4,5-dihydroisoxazol-3-yl}-1-cyclopentyl-3-methyl-1H-indazole (Compound No. 17),
1-Cyclopentyl-6-{5-[3-(2,4-difluorophenyl)-1,2,4-oxadiazol-5-yl]-5-methyl-4,5-dihydroisoxazol-3-yl}-3-methyl-1H-indazole (Compound No. 18),
1-Cyclopentyl-6-{5-[3-(2,3-difluorophenyl)-1,2,4-oxadiazol-5-yl]-5-methyl-4,5-dihydroisoxazol-3-yl}-3-methyl-1H-indazole (Compound No. 19),
1-Cyclopentyl-6-{5-[3-(2,4-dimethoxyphenyl)-1,2,4-oxadiazol-5-yl]-5-methyl-4,5-dihydroisoxazol-3-yl}-3-methyl-1H-indazole (Compound No. 20),
1-Cyclopentyl-6-{5-[3-(2,5-dimethoxyphenyl)-1,2,4-oxadiazol-5-yl]-5-methyl-4,5-dihydroisoxazol-3-yl}-3-methyl-1H-indazole (Compound No. 21),
1-Cyclopentyl-6-{5-[3-(2,5-dichlorophenyl)-1,2,4-oxadiazol-5-yl]-5-methyl-4,5-dihydroisoxazol-3-yl}-3-methyl-1H-indazole (Compound No. 22),
1-Cyclopentyl-6-{5-[3-(2,5-difluorophenyl)-1,2,4-oxadiazol-5-yl]-5-methyl-4,5-dihydroisoxazol-3-yl}-3-methyl-1H-indazole (Compound No. 23),
1-Cyclopentyl-6-{5-[3-(3,4-difluorophenyl)-1,2,4-oxadiazol-5-yl]-5-methyl-4,5-dihydroisoxazol-3-yl}-3-methyl-1H-indazole (Compound No. 24), 1-Cyclopentyl-6-{5-[3-(2,3-dimethoxyphenyl)-1,2,4-oxadiazol-5-yl]-5-methyl-4,5-dihydroisoxazol-3-yl}-3-methyl-1H-indazole (Compound No. 25), 6-{5-[3-(2-Chlorophenyl)-1,2,4-oxadiazol-5-yl]-5-methyl-4,5-dihydroisoxazol-3-yl}-1-cyclopentyl-3-ethyl-1H-indazole (Compound No. 26), 1-Cyclopentyl-6-{5-[3-(2,4-difluorophenyl)-1,2,4-oxadiazol-5-yl]-5-methyl-4,5-dihydroisoxazol-3-yl}-3-ethyl-1H-indazole (Compound No. 27), 1-Cyclopentyl-6-{5-[3-(2,3-difluorophenyl)-1,2,4-oxadiazol-5-yl]-5-methyl-4,5-dihydroisoxazol-3-yl}-3-ethyl-1H-indazole (Compound No. 28), 1-Cyclopentyl-6-{5-[3-(2,4-dimethoxyphenyl)-1,2,4-oxadiazol-5-yl]-5-methyl-4,5-dihydroisoxazol-3-yl}-3-ethyl-1H-indazole (Compound No. 29), 1-Cyclopentyl-6-{5-[3-(2,5-dimethoxyphenyl)-1,2,4-oxadiazol-5-yl]-5-methyl-4,5-dihydroisoxazol-3-yl}-3-ethyl-1H-indazole (Compound No. 30), 1-Cyclopentyl-6-{5-[3-(2,5-dichlorophenyl)-1,2,4-oxadiazol-5-yl]-5-methyl-4,5-dihydroisoxazol-3-yl}-3-ethyl-1H-indazole (Compound No. 31), 1-Cyclopentyl-6-{5-[3-(2,5-difluorophenyl)-1,2,4-oxadiazol-5-yl]-5-methyl-4,5-dihydroisoxazol-3-yl}-3-ethyl-1H-indazole (Compound No. 32), 1-Cyclopentyl-6-{5-[3-(3,4-difluorophenyl)-1,2,4-oxadiazol-5-yl]-5-methyl-4,5-dihydroisoxazol-3-yl}-3-ethyl-1H-indazole (Compound No. 33), 1-Cyclopentyl-6-{5-[3-(2,3-methoxyphenyl)-1,2,4-oxadiazol-5-yl]-5-methyl-4,5-dihydroisoxazol-3-yl}-3-ethyl-1H-indazole (Compound No. 34), 1-Cyclopentyl-6-{5-[5-(3,5-difluorophenyl)-1,2,4-oxadiazol-3-yl]-5-methyl-4,5-dihydroisoxazol-3-yl}-3-methyl-1H-indazole (Compound No. 35), 1-Cyclopentyl-6-{5-[5-(3,5-dimethoxyphenyl)-1,2,4-oxadiazol-3-yl]-5-methyl-4,5-dihydroisoxazol-3-yl}-3-methyl-1H-indazole (Compound No. 36)

1-Cyclopentyl-6-{5-[5-(4-fluorophenyl)-1,2,4-oxadiazol-3-yl]-5-methyl-4,5-dihydroisoxazol-3-yl}-3-methyl-1H-indazole (Compound No. 37), 6-{5-[5-(4-Chlorophenyl)-1,2,4-oxadiazol-3-yl]-5-methyl-4,5-dihydroisoxazol-3-yl}-1-cyclopentyl-3-methyl-1H-indazole (Compound No. 38), 1-Cyclopentyl-6-{5-[5-(2-fluorophenyl)-1,2,4-oxadiazol-3-yl]-5-methyl-4,5-dihydroisoxazol-3-yl}-3-methyl-1H-indazole (Compound No. 39), 1-Cyclopentyl-3-methyl-6-[5-methyl-5-(5-pyridin-4-yl-1,2,4-oxadiazol-3-yl)-4,5-dihydroisoxazol-3-yl]-1H-indazole (Compound No. 40), Methyl 3-(1-cyclopentyl-3-methyl-1H-indazol-6-yl)-5-methyl-4,5-dihydroisoxazole-5-carboxylate (Compound No. 41), 3-(1-Cyclopentyl-3-methyl-1H-indazol-6-yl)-5-methyl-4,5-dihydroisoxazole-5-carboxylic acid (Compound No. 42),

[3-(1-Cyclopentyl-3-methyl-1H-indazol-6-yl)-5-methyl-4,5-dihydroisoxazol-5-yl]methanol (Compound No. 43), Methyl 3-(1-cyclopentyl-3-methyl-1H-indazol-6-yl)-5-(2-methoxy-2-oxoethyl)-4,5-dihydroisoxazole-5-carboxylate (Compound No. 44), 5-(Carboxymethyl)-3-(1-cyclopentyl-3-methyl-1H-indazol-6-yl)-4,5-dihydroisoxazole-5-carboxylic acid (Compound No. 45), Methyl 3-(1-cyclopentyl-3-ethyl-1H-indazol-6-yl)-5-methyl-4,5-dihydroisoxazole-5-carboxylate (Compound No. 46), 3-(1-Cyclopentyl-3-ethyl-1H-indazol-6-yl)-5-methyl-4,5-dihydroisoxazole-5-carboxylic acid (Compound No. 47),

[3-(1-Cyclopentyl-3-ethyl-1H-indazol-6-yl)-5-methyl-4,5-dihydroisoxazol-5-yl]methanol (Compound No. 48), Methyl 3-(1-cyclopentyl-3-ethyl-1H-indazol-6-yl)-5-(2-methoxy-2-oxoethyl)-4,5-dihydroisoxazole-5-carboxylate (Compound No. 49), 5-(Carboxymethyl)-3-(1-cyclopentyl-3-ethyl-1H-indazol-6-yl)-4,5-dihydroisoxazole-5-carboxylic acid (Compound No. 50), 3-(1-Cyclopentyl-3-methyl-1H-indazol-6-yl)-N,5-dimethyl-4,5-dihydroisoxazole-5-carboxamide (Compound No. 51), 3-(1-Cyclopentyl-3-methyl-1H-indazol-6-yl)-5-methyl-N-propyl-4,5-dihydroisoxazole-5-carboxamide (Compound No. 52), 3-(1-Cyclopentyl-3-methyl-1H-indazol-6-yl)-N-cyclopropyl-5-methyl-4,5-dihydroisoxazole-5-carboxamide (Compound No. 53), 3-(1-Cyclopentyl-3-methyl-1H-indazol-6-yl)-N-methyl-5-[2-(methylamino)-2-oxoethyl]-4,5-dihydroisoxazole-5-carboxamide (Compound No. 54), 3-(1-Cyclopentyl-3-methyl-1H-indazol-6-yl)-5-[2-oxo-2-(propylamino)ethyl]-N-propyl-4,5-dihydroisoxazole-5-carboxamide (Compound No. 55), 3-(1-Cyclopentyl-3-methyl-1H-indazol-6-yl)-N-cyclopropyl-5-[2-(cyclopropylamino)-2-oxoethyl]-4,5-dihydroisoxazole-5-carboxamide (Compound No. 56), 3-(1-Cyclopentyl-3-ethyl-1H-indazol-6-yl)-N,5-dimethyl-4,5-dihydroisoxazole-5-carboxamide (Compound No. 57), 2-[3-(1-Cyclopentyl-3-ethyl-1H-indazol-6-yl)-5-methyl-4,5-dihydroisoxazol-5-yl]-N-propylacetamide (Compound No. 58), 3-(1-Cyclopentyl-3-ethyl-1H-indazol-6-yl)-N-cyclopropyl-5-methyl-4,5-dihydroisoxazole-5-carboxamide (Compound No. 59), 3-(1-Cyclopentyl-3-ethyl-1H-indazol-6-yl)-N-methyl-5-[2-(methylamino)-2-oxoethyl]-4,5-dihydroisoxazole-5-carboxamide (Compound No. 60), 3-(1-Cyclopentyl-3-ethyl-1H-indazol-6-yl)-5-[2-oxo-2-(propylamino)ethyl]-N-propyl-4,5-dihydroisoxazole-5-carboxamide (Compound No. 61), 3-(1-Cyclopentyl-3-ethyl-1H-indazol-6-yl)-N-cyclopropyl-5-[2-(cyclopropylamino)-2-oxoethyl]-4,5-dihydroisoxazole-5-carboxamide (Compound No. 62), Methyl 3-(3-ethyl-1-methyl-1H-indazol-6-yl)-5-(2-methoxy-2-oxoethyl)-4,5-dihydroisoxazole-5-carboxylate (Compound No. 63), Methyl 3-(1,3-dimethyl-1H-indazol-6-yl)-5-(2-methoxy-2-oxoethyl)-4,5-dihydroisoxazole-5-carboxylate (Compound No. 64), Methyl 3-(1-cyclopentyl-1H-indazol-6-yl)-5-methyl-4,5-dihydroisoxazole-5-carboxylate (Compound No. 65), Methyl 3-(1-cyclopentyl-1H-indazol-6-yl)-5-(2-methoxy-2-oxoethyl)-4,5-dihydroisoxazole-5-carboxylate (Compound No. 66), 3-(1-Cyclopentyl-3-ethyl-1H-indazol-5-yl)-5-methyl-4,5-dihydroisoxazole-5-carbonitrile (Compound No. 67), or 1-Cyclopentyl-6-{5-[5-(2,6-difluorophenyl)-1,2,4-oxadiazol-3-yl]-5-methyl-4,5-dihydroisoxazol-3-yl}-3-ethyl-1H-indazole (Compound No. 68).

3. A pharmaceutical composition comprising a therapeutically effective amount of a compound of claim 1 together with a pharmaceutically acceptable carrier, excipient or diluent.

* * * * *

UNITED STATES PATENT AND TRADEMARK OFFICE
CERTIFICATE OF CORRECTION

PATENT NO. : 7,781,460 B2
APPLICATION NO. : 12/065819
DATED : August 24, 2010
INVENTOR(S) : Venkata Palle et al.

Page 1 of 2

It is certified that error appears in the above-identified patent and that said Letters Patent is hereby corrected as shown below:

In the Specification

Column 3, line 17, please delete "TV" and replace with -- IV --

Column 4, line 49, please delete "-C(=O)NR$_x$R$_y$, -OC(-O)NR$_x$R$_y$" and replace with -- -C(=O)NR$_x$R$_y$, -OC(=O)NR$_x$R$_y$ --

Column 4, line 55, please add a "," in between "-NHR$_x$ -NH$_2$," to read as -- -NHR$_x$, -NH$_2$, --

Column 7 and 8, Line 1-34 Scheme I should read:

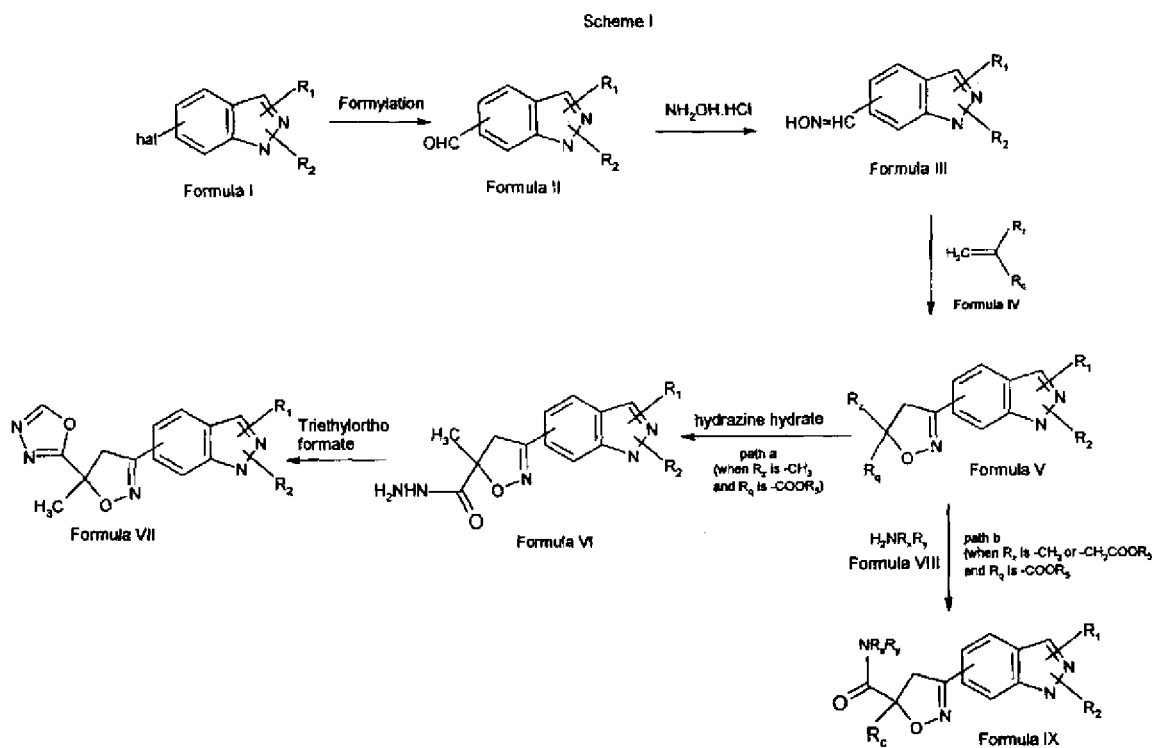

Signed and Sealed this
Eleventh Day of February, 2014

Michelle K. Lee
*Deputy Director of the United States Patent and Trademark Office*

CERTIFICATE OF CORRECTION (continued)
U.S. Pat. No. 7,781,460 B2

Column 10, Line 1-34 Scheme II should read:

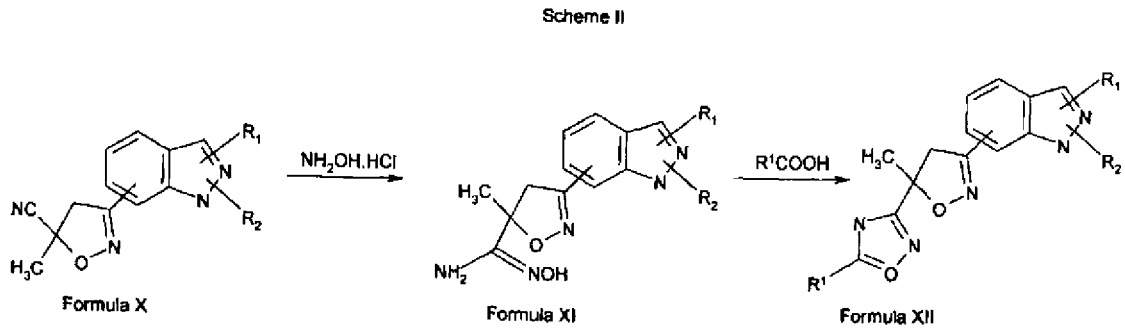

Columns 11 and 12, Line 8-42 Scheme III should read:

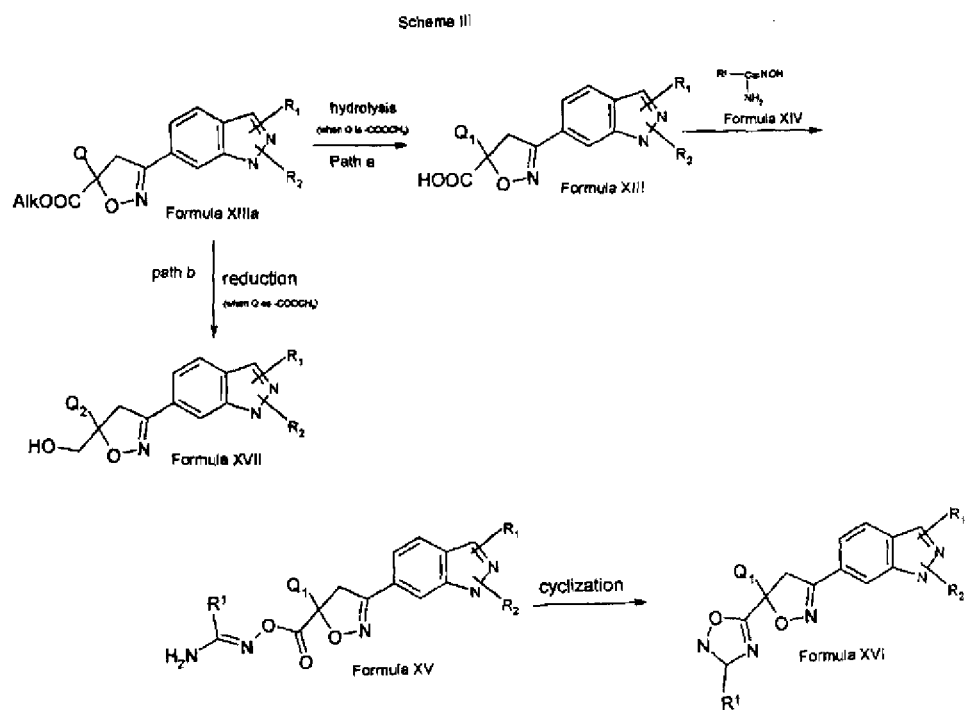

Column 16, lines 25 and 33, correct "methoxy-2-oxoethyl-4,5-dihydroisoxazole-5-carboxylate" to read as -- methoxy-2-oxoethyl)-4,5-dihydroisoxazole-5-carboxylate --

Column 16, line 46, correct "Mass (1-m/z)" to read as -- Mass (m/z) --

Column 17, line 50, correct "11.0 ml" to read as -- 1.0 ml --

Column 18, line 9, correct "(propylamino-ethyl]" to read as -- (propylamino)ethyl] --

Column 20, line 38, correct "(Compound 42" to read as -- (Compound 42) --

Column 22, line 11, correct "(Compound 31" to read as -- (Compound 31) --